(12) United States Patent
O'Neil

(10) Patent No.: US 8,470,769 B2
(45) Date of Patent: Jun. 25, 2013

(54) METHOD OF TREATMENT OF BACTERIAL INFECTION BY ADMINISTRATION OF POLY-LYSINE

(75) Inventor: Deborah O'Neil, Inverurie (GB)

(73) Assignee: Novabiotics, Ltd., Aberdeen (GB)

( * ) Notice: Subject to any disclaimer, the term of this patent is extended or adjusted under 35 U.S.C. 154(b) by 0 days.

(21) Appl. No.: 13/308,479

(22) Filed: Nov. 30, 2011

(65) Prior Publication Data

US 2012/0071398 A1    Mar. 22, 2012

Related U.S. Application Data

(60) Division of application No. 12/893,663, filed on Sep. 29, 2010, now Pat. No. 8,088,888, and a division of application No. 11/573,770, filed on Feb. 15, 2007, now Pat. No. 7,847,059, which is a continuation of application No. PCT/GB2005/003245, filed on Aug. 18, 2005, which is a continuation of application No. 11/079,795, filed on Mar. 14, 2005, now abandoned.

(30) Foreign Application Priority Data

Aug. 18, 2004    (GB) .................................. 0418414.9

(51) Int. Cl.
| | | |
|---|---|---|
| A61P 31/04 | (2006.01) | |
| A61K 38/00 | (2006.01) | |
| A61K 38/16 | (2006.01) | |
| C07K 14/00 | (2006.01) | |
| C07K 14/47 | (2006.01) | |
| A01N 37/04 | (2006.01) | |

(52) U.S. Cl.
USPC .............. 514/2.2; 514/2.4; 514/2.7; 530/350

(58) Field of Classification Search
None
See application file for complete search history.

(56) References Cited

U.S. PATENT DOCUMENTS

| 5,696,078 A | 12/1997 | Oppenheim et al. ............ 514/2 |
| 5,714,577 A | 2/1998 | Montelaro et al. ............ 530/324 |
| 7,482,328 B2 | 1/2009 | Yoshida et al. .............. 514/1.1 |
| 2002/0001582 A1 | 1/2002 | Charter et al. ............... 424/94.6 |
| 2003/0087827 A1 | 5/2003 | Lindberg et al. |
| 2003/0208035 A1 | 11/2003 | Dimarcq et al. ............. 530/324 |

FOREIGN PATENT DOCUMENTS

| EP | 0502718 A1 | 9/1992 |
| EP | 00502718 A1 | 9/1992 |
| EP | 1502949 A1 | 2/2005 |
| JP | 2005-035914 | * 2/2005 |
| WO | 9840401 A2 | 9/1998 |
| WO | WO/03/091429 | 11/2003 |

OTHER PUBLICATIONS

Machine translation of JP2005-035914—Apr. 8, 2011.*
Dorland's Medical Dictionary, 30th edition, p. 2 and 498, Elsevier, ISBN 0-7126-0146-4, 2003.
Weitzman et al., The Dermatophytes. Clin. Microbiol. Rev., 8, 240-259. 1995.
Shima et al., Antimicrobial action of ε-poly-L-Lysine, J. Antibio. 37, 1449-1455, 1984.
Haynie, Sharon L. et al., "Antimicrobial Activities of Amphiphilic Peptides Covalently Bonded to a Water-Insoluble Resin," Antimicrobial Agents and Chemotherapy, American Society for Microbiology, vol. 39, No. 2, pp. 301-307 (Feb. 1995).
Miller, Chandra T. et al., "The Synthesis and Screening of 1,4,5,8-Naphthalenetetracarboxylic Diimide—Peptide Conjugates with Antibacterial Activity," Bioorganic & Medicinal Chemistry, vol. 9, pp. 2015-2024 (2001).
Bessalle, Roberto et al., "Augmentation of the Antibacterial Activity of Magainin by Positive-Charge Chain Extension," Antimicrobial Agents and Chemotherapy, American Society for Microbiology, vol. 36, No. 2, pp. 313-317 (Feb. 1992).
Zasloff, Michael, "Antimicrobial peptides of multicellular organisms," Nature, vol. 415, pp. 389-395 (Jan. 24, 2002).
Helmerhorst, Eva J. et al., "Synthetic histatin analogues with broad-spectrum antimicrobial activity," Biochem. J., vol. 326, pp. 39-45 (1997).

* cited by examiner

*Primary Examiner* — Elly-Gerald Stoica
(74) *Attorney, Agent, or Firm* — Janet Sleath; Speckman Law Group PLLC

(57) ABSTRACT

The present invention relates to peptides comprising amino acids according to Formula I $$((X)_l(Y)_m)_n \quad (I)$$

wherein l, m and n are integers from 0 to 10; X and Y, which may be the same or different, are an amino acid selected from the group consisting of hydrophobic amino acids and/or cationic amino acids, together with methods for the use of the peptides in the treatment of microbial infections.

16 Claims, 17 Drawing Sheets

Figure 1

Peptide 1     +9.24 Hydrophobicity          0 Net charge

GGGGGGGCGGGGGGCGGGGCGGGGGGGGGCGGGGGGCCGG

Peptide 2     +67.04 Hydrophobicity         0 Net charge

LLLLLLLCLLLLLLLCLLLLCLLLLLLLLLLCLLLLLLLCCLL

Peptide 3     +38.14 Hydrophobicity         0 Net charge

GLGLGLGCLGLGLGCGLGLCLGLGLGLGLCGLGLGLCCLG

Peptide 4     -27.64 Hydrophobicity     +36 Net charge

KRKRKRKCRKRKRRCRKRKCKRKRKRKRKCRKRKRKCCRRKK

Effect of acetic acid on growth of *T. interdigitale*

Effect of reduced concentration (100μg/ml) of polyarginine
on *T. rubrum* and *T. interdigitale*

METHOD OF TREATMENT OF BACTERIAL INFECTION BY ADMINISTRATION OF POLY-LYSINE

REFERENCE TO RELATED APPLICATIONS

This application is a divisional of U.S. patent application Ser. No. 12/893,663, filed Sep. 29, 2010, now U.S. Pat. No. 8,088,888, which is a divisional of U.S. patent application Ser. No. 11/573,770, filed Feb. 15, 2007, now U.S. Pat. No. 7,847,059, which is a continuation of International Patent Application No. PCT/GB2005/003245, flied Aug. 18, 2005, which claims priority to U.S. patent application Ser. No. 11/079,795 filed Mar. 14, 2005, now abandoned, and United Kingdom Patent Application. No 0418414.9, filed Aug. 18, 2004.

FIELD OF THE INVENTION

The present invention provides antimicrobial peptides. The invention further relates to pharmaceutical compositions comprising the antimicrobial peptides and the use of the peptides in the treatment of, inter alia, microbial infections.

BACKGROUND OF THE INVENTION

One major family of endogenous antibacterial peptides, the beta-defensins, are secreted by the epithelial cells that line the digestive, respiratory and urogenital tracts of higher mammals. They are also produced by keratinocytes within the skin. Their primary role is to provide an essential first line of defense against infection via these routes by pathogenic organisms.

The defensins are one of the most studied classes of antimicrobial peptides. This class consists of cysteine-rich molecules with three disulphide bridges. They are found in plants, insects and various mammals. In humans, two classes of defensin are found which differ from one another in terms of spacing and bonds between the six cysteine residues. The first of these classes is the alpha-defensins (six types) that have been isolated from neutrophils (HNP1-4, human neutrophil peptide) and in the paneth cells of the gastrointestinal tract (alpha-defensins 5 and 6). The second class, the beta-defensins, are longer, more basic, and are expressed throughout the mucosae within the epithelial cells and keratinocytes that line and/or comprise and/or are present within the digestive, respiratory and urogenital tracts, and the skin. hBD1 (human beta-defensin 1) is secreted constitutively and human beta-defensins 2, 3 and 4 (hBD2, hBD3 and hBD4) are produced in response to infection or inflammation. hBD2 expression and secretion is triggered by bacterial stimulation, particularly flagellated bacteria (Harder et al, Nature 1997; 387:861), and IL1α and IL1β (Liu et al, J. Invest. Dermatol. 2002; 118; 275-281). In some tissue sites, Tumor Necrosis Factor alpha (TNF-alpha) and Lipopolysaccharide (LPS) may also play a role in inducing hBD2 expression. In vitro experiments have revealed that hBD2 is active against Gram negative bacteria such as *Escherichia coli* (*E. coli*) and to a lesser extent, Gram positive bacteria such as *Streptococcus pneumoniae* (*Str. pneumoniae*). hBD2 also demonstrates killing activity in vitro against the yeast *Candida albicans*. hBD3 expression and secretion is induced by bacterial stimulation, TNF-alpha and especially Interferon-gamma (IFNγ) which also have the common property of being molecules involved in inflammatory processes.

In addition to the potent, constitutive and regulated broad-spectrum innate antimicrobial protection that the beta-defensins provide, these molecules, hBD2 in particular, also have the ability to mobilize the adaptive arm of the immune response through chemotactic effects on immature dendritic cells and memory T-lymphocytes (Yang et al, Science 1999; 286: 525-528).

Importantly, evidence is coming to light that beta-defensins not only provide defense against infection from pathogenic microbes, but are key in regulating and maintaining optimal density and diversity of the body's essential commensal microbial ecosystems, such as those on the skin, and within the gastrointestinal and genital tracts (Ganz, T, Nat. Rev. Immunol. 2003 3(9): 710-20).

The mode of action of beta-defensins is such that they are largely non-toxic to host cells at active concentrations. The beta-defensins have, therefore, been implicated as potential targets for therapeutics for a wide range of infections. However, natural forms of defensins are technically challenging to produce in recombinant systems resulting in low yields. Moreover, evidence is growing to suggest that, through their chemotactic actions, beta-defensins are potent inflammatory compounds (Yang et al, Science 1999; 286: 525-528; Van Wetering et al., Inflamm. Res. 2002; 51(1): 8-15; Niyonsaba et al. Curr. Drug Targets Inflamm. Allergy 2003; 2(3): 224-231). Taken together, these factors make natural defensins unsuitable for therapeutic applications.

Beta-defensins are also highly salt sensitive (Porter et al., Infect. Immun. 1997; 65(6): 2396-401; Bals et al., J. Clin. Invest. 1998; 102(5): 874-80; Valore et al., J. Clin. Invest. 1998; 101(8): 1633-42; Goldmann et al., Cell 1997; 88(4): 553-609; Singh et al., Proc. Natl. Acad. Sci. USA 95(25): 14961-6). For this reason, beta-defensins cannot provide antimicrobial protection in conditions such as cystic fibrosis wherein, although the respiratory epithelia produce abundant beta-defensins in response to the persistent bacterial infections associated with this condition, they are inactive due to the imbalance in ion transport across the respiratory epithelial membranes that results in increased cation resorption (Na+ in particular) and increased chloride secretion (Donaldson S H and Boucher R C. Curr. Opin. Pulm. Med. 2003 November; 9(6):486-91; Davies J C. Pediatr. Pulmonol. Suppl. 2004; 26:147-8.)

There is a requirement, therefore, for further agents that can be used to treat microbial infections.

SUMMARY OF THE INVENTION

The present inventors have identified peptides that, surprisingly, have improved antimicrobial activity over natural defensins.

According to a first aspect of the invention, there is provided a peptide comprising from 3 to about 200 D and/or L amino acids, which may be the same or different, wherein the amino acids are selected from the group consisting of hydrophobic amino acids and/or cationic amino acids. The peptide may comprise 3 to about 100 D and/or L amino acids, for example 3 to 50 D and/or L amino acids including 4 to about 50 D and/or L-amino acids. The peptides of the invention are useful, inter alia, in the treatment or prevention of microbial infections.

In a further aspect of the invention there is provided a peptide comprising amino acids according to the formula I:

$$((X)_l(Y)_m)_n \quad (I)$$

wherein l and m are integers from 0 to 10, for example 0 to 5; n is an integer from 1 to 10; X and Y, which may be the same or different, are an amino acid selected from the group consisting of hydrophobic amino acids and/or cationic amino acids.

In a preferred aspect of the invention, the peptide comprises from 3 to 200 amino acids, for example 3, 4, 5, 6 or 7 up to 100 amino acids, including 3, 4, 5, 6, or 7 up to 20, 25, 30, 35, 40 or 42 amino acids.

The peptide according to the invention may comprise 100 to 200 amino acids, 27 to 100 amino acids, 28 to 86 amino acids, 7 to 27 amino acids or 3 to 14 amino acids.

Preferably the peptides comprise 3 to 15 amino acids, for example 3 to 7 amino acids.

In a further preferred aspect, the peptides comprise one or more cysteine residues, for example up to 6 cysteine residues, such as 1, 2, 3, 4, 5 or 6 cysteine residues.

In a preferred aspect of the invention, there is provided a peptide comprising amino acids according to the Formula II:

$$C((X)_l(Y)_m)_nC((X)_l(Y)_m)_n \qquad (II)$$

wherein C is cysteine, l, n and m are an integer from 0 to 10; and X and Y, which may be the same or different, are an amino acid selected from the group consisting of hydrophobic amino acids and/or cationic amino acids.

In a further preferred aspect of the invention, the peptide comprises amino acids according to the Formula III:

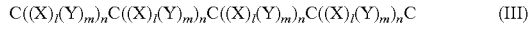

$$C((X)_l(Y)_m)_nC((X)_l(Y)_m)_nC((X)_l(Y)_m)_nC((X)_l(Y)_m)_nC \qquad (III)$$

wherein C, X, Y, l, m and n are as defined herein.

In a yet further preferred aspect of the invention, the peptide comprises amino acids according to the Formula IV

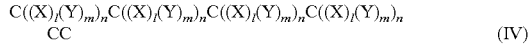

$$\begin{array}{c}C((X)_l(Y)_m)_nC((X)_l(Y)_m)_nC((X)_l(Y)_m)_nC((X)_l(Y)_m)_n\\CC\end{array} \qquad (IV)$$

wherein C, X, Y, l, m and n are as defined herein.

Since the peptides of the invention are simpler in structure than natural beta-defensins, they are simple and efficient to produce. The peptides are also substantially salt insensitive and are not hepatotoxic. Moreover, their mode of action, being physical rather than metabolic (i.e. direct membrane disruption versus targeting components of vital metabolic pathways), minimizes, if not rules out, the probability that target microbes can develop resistance to these antimicrobial agents.

As known to the skilled person, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. As used herein, the terms "hydrophobic" and "cationic" may refer to amino acids having a hydrophobicity that is greater than or equal to −1.10 and/or a net charge that is greater than or equal to 0 as described in Fauchere and Pliska, Eur. J. Med. Chem. 10:39 (1983). A hydrophobic or nonpolar amino acid may also refer to an amino acid having a side chain that is uncharged at physiological pH, that is not polar and that is generally repelled by aqueous solution.

In a preferred aspect of the invention, X and/or Y are selected from the group of hydrophobic amino acids consisting of glycine, leucine phenylalanine, proline, alanine, tryptophan, valine, isoleucine, methionine, tyrosine and threonine, and/or the group of cationic amino acids consisting of ornithine, histidine, arginine and lysine. X and/or Y may be D or L-amino acids. Moreover, X and/or Y may be alternating amino acids.

The invention also includes known isomers (structural, stereo-, conformational and/or configurational) and structural analogues of the above amino acids, and those modified either naturally (e.g. post-translational modification) or chemically, including, but not exclusively, phosphorylation, glycosylation, sulfonylation and/or hydroxylation.

In general, the peptides of the invention do not include the amino acids aspartic acid, glutamic acid, asparagine, glutamine or serine, but certain peptides of the invention may have activity even though these amino acids are present.

The peptides of the invention may include one or more additional amino acid residues adjacent to one or both of the terminal cysteine residues of formula II, III or IV, for example, the peptides may comprise up to 10 (for example 1, 2, 3, 4, 5, 6, 7, 8, 9 or 10) additional amino acid residues. Preferably, the additional amino acids are non-cysteine residues. More preferably, the additional amino acids are X and/or Y.

In addition, the amino acid sequence of a peptide can be modified so as to result in a peptide variant that includes the substitution of at least one amino acid residue in the peptide for another amino acid residue, including substitutions that utilize the D rather than L form.

One or more of the residues of the peptide can be exchanged for another to alter, enhance or preserve the biological activity of the peptide. Such a variant can have, for example, at least about 10% of the biological activity of the corresponding non-variant peptide. Conservative amino acids are often utilized, i.e. substitutions of amino acids with similar chemical and physical properties as described above.

Hence, for example, conservative amino acid substitutions may involve exchanging lysine for arginine, ornithine or histidine; exchanging one hydrophobic amino acid for another. After the substitutions are introduced, the variants are screened for biological activity.

The peptide may comprise at least 4 amino acids, for example, between 4 and 50 amino acids, or 4 and 50 amino acids, such as between 20 and 45 amino acids such as 20, 25, 30, 35, 40, 42 or 45 amino acids.

In a preferred aspect of the invention, X and Y are the same and are leucine or glycine.

In a further preferred aspect of the invention, X is leucine and Y is glycine.

In a further preferred aspect, X and Y are the same and are lysine or arginine. Thus the invention provides peptides selected from poly-L-lysine, poly-D-lysine, poly-L-arginine and poly-D-arginine.

In a yet further preferred aspect, X is lysine and Y is arginine.

In the peptide of the invention l and m may be 0, 1, 2, 3, 4, 5, 6, 7, 8, 9 or 10 and n may be 1, 2, 3, 4, 5, 6, 7, 8, 9 or 10.

In the peptide of the invention l may be 1, n may be 1 and m may be between 4 and 9, for example, m may be 3, 4, 5, 6, 7, 8 or 9.

In the peptide of the invention l, n and/or m may be between 1 and 5, for example, 1, 2, 3, 4 or 5.

Preferably the peptide is acyclic. The peptide may be straight chained, i.e. linear, or branched.

The term "peptide" as used herein means, in general terms, a plurality of amino acid residues joined together by peptide bonds. It is used interchangeably and means the same as polypeptide and protein.

In one embodiment of the invention, the peptide comprises an amino acid sequence selected from the group consisting of:

| | | |
|---|---|---|
| CGGGGGGCGGGGCGGGGGGGGCGGGGG GCC | (i) | (SEQ ID NO: 1) |
| CLLLLLLCLLLLCLLLLLLLLLCLLLLL LCC | (ii) | (SEQ ID NO: 2) |
| CLGLGLGCGLGLCLGLGLGLGLCGLGLG LCC | (iii) | (SEQ ID NO: 3) |
| CRKRKRRCRKRKCKRKRKRKRKCRKRKR KCC | (iv) | (SEQ ID NO: 4) |
| KKK | (v) | |
| KKKKKKK | (vi) | (SEQ ID NO: 5) |
| RRR | (vii) | |
| RRRRRRR | (viii) | (SEQ ID NO: 6) |

In a further aspect of the invention, the peptide comprises at least one of the amino sequences (i) to (viii) and additional amino acid residues adjacent to one or both of the terminal cysteine residues. Thus, in a further embodiment of the invention there is provided a peptide comprising an amino acid sequence selected from the amino acid sequences shown in FIG. 1 (SEQ ID NO: 7-10, referred to as Peptides 1-4, respectively).

The peptides of the invention generally are synthetic peptides. The peptides may be isolated, purified peptides or variants thereof, which can be synthesized in vitro, for example, by a solid phase peptide synthetic method, by enzyme catalyzed peptide synthesis or with the aid of recombinant DNA technology.

To identify active peptides that have little or no undesired toxicity for mammalian cells, individual peptides, or libraries of peptides, can be made and the individual peptides or peptides from those libraries can be screened for antimicrobial activity and toxicity, including, but not limited to, antifungal, antibacterial, antiviral, antiprotozoal, anti-parasitic activity and toxicity.

The peptides of the invention can exist in different forms, such as free acids, free bases, esters and other prodrugs, salts and tautomers, for example, and the invention includes all variant forms of the compounds.

Thus, the invention encompasses the salt or pro-drug of a peptide or peptide variant of the invention.

The peptides of the invention may be administered in the form of pharmaceutically acceptable salts. The pharmaceutically acceptable salts of the present invention can be synthesized from the parent peptide which contains a basic or acidic moiety by conventional chemical methods. Generally, such salts can be prepared by reacting the free acid or base forms of these peptides with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002.

The invention thus includes pharmaceutically-acceptable salts of the disclosed peptides wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Salts of carboxyl groups of a peptide or peptide variant of the invention may be prepared in the usual manner by contacting the peptide with one or more equivalents of a desired base such as, for example, a metallic hydroxide base, e.g. sodium hydroxide; a metal carbonate or bicarbonate such as, for example, sodium carbonate or bicarbonate; or an amine base such as, for example, triethylamine, triethanolamine and the like.

N-acyl derivatives of an amino group of the peptide or peptide variants of the invention may be prepared by utilizing an N-acyl protected amino acid for the final condensation, or by acylating a protected or unprotected amino acid. O-acyl derivatives may be prepared, for example, by acylation of a free hydroxy peptide or peptide resin. Either acylation may be carried out using standard acylating reagents such as acyl halides, anhydrides, acyl imidazoles, and the like.

The invention includes prodrugs for the active pharmaceutical species of the described peptides, for example in which one or more functional groups are protected or derivatized but can be converted in vivo to the functional group, as in the case of esters of carboxylic acids convertible in vivo to the free acid, or in the case of protected amines, to the free amino group. The term "prodrug," as used herein, represents in particular structures which are rapidly transformed in vivo to the parent structure, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins et al., Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. acyloxyalkyl esters, amides |
| Alcohol | Esters, including e.g. sulfates and phosphates as well as carboxylic acid esters |
| Amine | Amides, carbamates, imines, enamines, |
| Boronic acid | Diol ester |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:
  Oxidative Activation
  N- and O-dealkylation
  Oxidative deamination
  N-oxidation
  Epoxidation
  Reductive Activation
  Azo reduction
  Sulfoxide reduction
  Disulfide reduction
  Bioreductive alkylation
  Nitro reduction.

Also to be mentioned as metabolic activations of prodrugs are nucleotide activation, phosphorylation activation and decarboxylation activation.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Thus, it will be appreciated by those skilled in the art that, although protected derivatives of the described peptides may not possess pharmacological activity as such, they may be administered, for example parenterally or orally, and thereafter metabolized in the body to form compounds which are pharmacologically active. Such derivatives are therefore examples of "prodrugs". All prodrugs of the described compounds are included within the scope of the invention.

A further aspect of the invention provides a pharmaceutical composition comprising a pharmaceutically effective amount of at least one of the peptides of the invention, or two or more different peptides of the invention.

These peptides also include a pharmaceutically acceptable carrier, excipient or diluent. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The peptides of the invention are useful, inter alia, as antimicrobial peptides, for example, against bacteria, fungi, yeast, parasites, protozoa and viruses. The term, "antimicrobial peptide" can be used herein to define any peptide that has microbicidal and/or microbistatic activity and encompasses, non-exclusively, any peptide described as having anti-bacterial, anti-fungal, anti-mycotic, anti-parasitic, anti-protozoal, anti-viral, anti-infectious, anti-infective and/or germicidal, algicidal, amoebicidal, microbicidal, bacterici(o)dal, fungicidal, parasiticidal, protozoacidal, protozoicidal properties.

Thus, the invention further provides a peptide according to the invention for use as a medicament. The peptides of the invention may have application as antimicrobial agents both in vivo and ex vivo.

In a preferred aspect, the invention provides the use of a peptide according to the invention in the manufacture of a medicament for treating a microbial infection.

By "microbial infection" is meant an infection caused by a bacterial, parasitic, protozoan, viral or fungal pathogen. A "pathogen" is generally defined as any disease-causing organism.

A bacterial pathogen may be derived from a bacterial species selected from the group consisting of: *Staphylococcus* spp., e.g. *Staphylococcus aureus, Staphylococcus epidermidis; Enterococcus* spp., e.g. *Enterococcus faecalis; Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptoccocus pneumoniae; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella tularensis; Bacillus* spp., e.g. *Bacillus anthracis; Clostridia* spp., e.g. *Clostridium botulinum; Yersinia* spp., e.g. *Yersinia pestis; Treponema* spp.; and *Burkholderia* spp.; e.g. *Burkholderia mallei* and *Burkholderia pseudomallei.*

A viral pathogen may be derived from a virus selected from the group consisting of: Human Immunodeficiency Virus (HIV1 & 2); Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus; hepatitis B and C viruses; Variola virus; rotavirus; and SARS coronavirus.

A parasitic pathogen may be derived from a parasitic pathogen selected from the group consisting of *Trypanosoma* spp. (*Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp., *Crytosporidium* spp., *Isospora* spp., *Balantidium* spp., *Loa Loa, Ascaris lumbricoides, Dirofilaria immitis*, and *Toxoplasma* ssp., e.g *Toxoplasma gondii.*

A fungal pathogen may be derived from a fungal pathogen which is of the genus *Candida* spp., (e.g. *C. albicans*), *Epidermophyton* spp., *Exophiala* spp., *Microsporum* spp., *Trichophyton* spp., (e.g. *T. rubrum* and *T. interdigitale*), *Tinea* spp., *Aspergillus* spp., *Blastomyces* spp., *Blastoschizomyces* spp., *Coccidioides* spp., *Cryptococcus* spp., *Histoplasma* spp., *Paracoccidiomyces* spp., *Sporotrix* spp., *Absidia* spp., *Cladophialophora* spp., *Fonsecaea* spp., *Phialophora* spp., *Lacazia* spp., *Arthrographis* spp., *Acremonium* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphium* spp., *Leptosphaeria* spp., *Malassezia* spp., *Mucor* spp., *Neotestudina* spp., *Nocardia* spp., *Nocardiopsis* spp., *Paecilomyces* spp., *Phoma* spp., *Piedraia* spp., *Pneumocystis* spp., *Pseudallescheria* spp., *Pyrenochaeta* spp., *Rhizomucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Ulocladium* spp., *Ustilago* spp., *Verticillium* spp., or *Wangiella* spp.

The microbial infections treatable by the peptides of the present invention may be selected from any of the human bacterial, fungal, parasitic, and enveloped viral pathogens shown in Tables 1A-D below.

TABLE 1A

Non-exclusive list of Human Bacterial Pathogens

| Genus | Species | Comments |
|---|---|---|
| Abiotropha | defectiva | |
| | elegans | |
| Achromobacter | alcaligenes | |
| Acidaminococcus | fermentans | |
| Acinetobacter | baumannii | |
| | calcoaceticus | |
| | lowffii | |
| | haemolyticus | |
| Actinobacillus | actinomycetemcomitans | |
| Actinomadura | madurae | |
| | pelletieri | |
| | dassonvillei | |
| Actinomyces | israelii | |
| | gerencseriae | |
| | pyogenes | |
| | naeslundii | |
| | bernardiae | |
| | neuii | |
| | radingae | |
| | turicensis | |
| | propinicus | |
| Aerococcus | urinae | |
| | viridans | |
| Aeromonas | hydrophila | |
| | veroniae | |
| | caviae | |
| Alcaligenes | xylososidans | |
| | denitrificans | |
| | faecalis | |
| Anaerovibrio | lipolytica | |
| Arcanobacterium | pyogenes | |
| | haemolyticum | |
| Arthrobacter | globiformis | |
| | creatinolyticus | |
| | cumminsii | |
| | woluwensis | |
| Bacillus | anthracis | |
| | cereus | |
| | brevis | |
| | subtilis | |
| | licheniformis | |
| | macerans | |
| | alvei | |
| | megaterium | |
| | pumilis | |
| | coagulans | |
| | laterosporus | |
| | thuringiensis | |
| | sphaericus | |
| | circulans | |
| Bacteroides | fragilis | |
| | vulgatus | |
| | forsythus | |
| | buccae | |
| | gingivalis | |
| | ureolyticus | |
| | gracilis | |
| | tectum | |
| Bartonella | quintana | |
| | henselae | |
| | bacilliformis | |
| | washoensis | |
| | clarridgeiae | |
| | elizabethae | |
| Bordatella/ | avium | |
| Bordetella | hinzii | |
| | pertussis | |
| | parapertussis | |
| | bronchiseptica | |
| | petrii | |
| Borrelia | hermsii | |
| | turicatae | |
| | burgdorferi | |
| | recurrentis | |
| | duttonii | |
| | garinii | |
| | afzelii | |
| | japonica | |
| | andersonii | |
| Brachyspira | hyodysenteriae | |
| | pilosicoli | |
| Brucella | abortus | |
| | melitensis | |
| | suis | |
| | canis | |
| Burkholderia | mallei | |
| | cepacia | |
| | pseudomallei | |
| | multivorans | |
| | stabilis | |
| | gladioli | |
| | vietnamiensis | |
| | ambifaria | |
| | fungorum | |
| Calymmatobacterium | granulomatis | |
| Campylobacter | fetus | |
| | jejuni | |
| | coli | |
| | lari | |
| | hyointestinalis | |
| | mucosalis | |
| | concisus | |
| | sputorum | |
| | upsaliensis | |
| | curvus | |
| | rectus | |
| | hominis | |
| Capnocytophaga | canimorsus | |
| | gingivalis | |
| | ochracea | |
| | cynodegmi | |
| Cardiobacterium | hominis | |
| | vulvarum | |
| Catonella | morbi | |
| Chlamydia | trachomatis | |
| | pneumoniae | |
| | psittaci | |
| Chryseobacterium | meningosepticum | |
| Citrobacter | freundii | |
| | diversus | |
| Clostridium | botulinum | |
| | difficile | |
| | tetani | |
| | perfringens | |
| | butyricum | |
| | diphtheriae | |
| | sordellii | |
| | septicum | |
| | tertium | |
| | clostridioforme | |
| | inocuum | |
| | ramosum | |
| | coccoides | |
| Corynebacterium | diphtheriae | |
| | ulcerans | |
| | minutissimum | |
| | pseudotuberculosis | |
| | pseudodiphtheriticum | |
| | xerosis | |
| | jeikeium | |
| | parvum | |
| | macginleyi | |
| | amycolatum | |
| Coxiella | burnetii | |
| Dermabacter | hominis | |
| Desulfovibrio | desulfuricans | |
| | fairfieldensis | |
| | vulgaris | |
| | salexigens | |
| | africanus | |
| | gigas | |
| | baculatus | |

TABLE 1A-continued

Non-exclusive list of Human Bacterial Pathogens

| Genus | Species | Comments |
|---|---|---|
| | sapovorans | |
| | baarsii | |
| | thermophilus | |
| | gabonensis | |
| | piger | |
| | profundus | |
| | aosterae | |
| | burkinensis | |
| | longus | |
| | orale | |
| | aespoeensis | |
| Dialister | pneumocintes | |
| | invisus | |
| Dolosicoccus | paucivorans | |
| Dolosigranulum | pigrum | |
| Edwardsiella | tarda | |
| | hoshinae | |
| Eggerthella | lenta | |
| Ehrlichia | sennetsu | |
| | chaffeensis | |
| | phagocytophila | |
| | ewingii | |
| | canis | |
| Eikinella | corrodens | |
| Empedobacter | brevis | |
| Enterobacter | cloacae | |
| | agglomerans | |
| | aerogenes | |
| | sakazakii | |
| Enterococcus | faecalis | |
| | faecium | |
| | gallinarum | |
| | casseliflavus | |
| | flavescens | |
| | gilvus | |
| | hirae | |
| | pallens | |
| | raffinosus | |
| | solitarius | |
| Erysipelothrix | rhusiopathiae | |
| Escherichia | coli | |
| | fergusonii | |
| | taylorae | |
| | hermanii | |
| | vulneris | |
| Eubacterium | brachy | |
| | timidum | |
| | nodatum | |
| | saphenum | |
| | aerofaciens | |
| | lentum | |
| Facklamia | languida | |
| | sourekii | |
| | ignavia | |
| | hominis | |
| Filifactor | alocis | |
| | villosus | |
| Flavimonas | oryzihabitans | |
| Flavobacterium | meningosepticum | |
| | breve | |
| | scophthalmum | |
| | johnsoniae | |
| Fluoribacter | bozemaniae | |
| Francisella | tularensis | |
| | philomiragia | |
| Fusobacterium | necrophorum | |
| | nucleatum | |
| Gardnerella | vaginalis | |
| Gemella | morbillorum | |
| | haemolysans | |
| | bergeriae | |
| | sanguinis | |
| Globicatella | sanguis | |
| | sanguinius | |
| | sulfidifaciens | |

TABLE 1A-continued

Non-exclusive list of Human Bacterial Pathogens

| Genus | Species | Comments |
|---|---|---|
| Granulicatella | elegans | |
| | adiacens | |
| Haemophilus | influenzae | |
| | parainfluenzae | |
| | ducreyi | |
| | aegyptus | |
| | paraphrophilus | |
| | aphrophilus | |
| Hafnia | alvei | |
| Helicobacter | pylori | |
| | cinaedi | |
| | fennelliae | |
| | rappini | |
| | heilman(n)ii | |
| | pullorum | |
| | bilis | |
| | hepaticus | |
| | westmeadii | |
| | canadensis | |
| | typhlonius | |
| Helococcus | kunzii | |
| Ignavigranum | ruoffiae | |
| Inquilinus | limosus | |
| Kingella | kingae | |
| | dentrificans | |
| Klebsiella | pneumoniae | |
| | agglomerans | |
| | oxytoca | |
| Kytococcus | schroeteri | |
| Lactobacillus | rhamnosus | |
| Lactococcus | lactis | |
| Legionella | pneumophila | |
| | anisa | |
| | sainthelensi | |
| | birminghamensis | |
| | micdadei | |
| | dumofii | |
| | longbeachae | |
| | cincinattiensis | |
| | bozemanii | |
| | gormanii | |
| | macehenii | |
| | tusconensis | |
| | feelii | |
| | hackeliae | |
| | oakridgensis | |
| | lansingensis | |
| | israelensis | |
| | jordansis | |
| | wadsworthii | |
| Leptospira | biflexa | |
| | borgpetersenii | |
| | interrogans | |
| | kirschneri | |
| | noguchii | |
| | santarosai | |
| | weilii | |
| | wolbachii | |
| | inadai | |
| | meyeri | |
| | ivanovii | |
| Leptotrichia | amnionii | |
| | buccalis | |
| | sanguinegans | |
| Leuconostoc | mesenteroides | |
| | pseudomesenteroides | |
| Listeria | monocytogenes | |
| | ivanovii | |
| Megasphaera | micronuciformis | |
| | elsdenii | |
| Micrococcus | luteus | |
| Micropolyspora | faeni | |
| Mobiluncus | mulieris | |
| | curtisii | |
| Moraxella | lacunata | |
| | nonliquefaciens | |

TABLE 1A-continued

Non-exclusive list of Human Bacterial Pathogens

| Genus | Species | Comments |
|---|---|---|
| | catarrhalis | |
| | influenzae | |
| Morganella | morganii | |
| Mycobacterium | tuberculosis | |
| | ulcerans | |
| | avium | |
| | intracellulare | |
| | marin(ar)um | |
| | leprae | |
| | kansasii | |
| | scrofulaceum | |
| | chelonae | |
| | bovis | |
| | africanum | |
| | microtii | |
| | fortuitum | |
| | hominis | |
| | pneumoniae | |
| | malmoense | |
| | paratuberculosis | |
| | simiae | |
| | szulagi | |
| | xenopi | |
| Mycoplasma | pneumoniae | |
| | genitalium | |
| | hominis | |
| | pulmonis | |
| | caviae | |
| Myroides | odoratus | |
| | odoratimimus | |
| Neisseria | meningitides | |
| | gonorrhoeae | |
| | lactamica | |
| | mucosa | |
| Nocardia | caviae | |
| | asteroides | |
| | brasiliensis | |
| | vaccinii | |
| | africana | |
| | veterana | |
| | arthritidis | |
| | anaemiae | |
| | farcinica | |
| | nova | |
| | otitidiscaviarum | |
| Orientia | tsutsugamuchi | |
| Pandoraea | pneumonicola | |
| | sputorum | |
| | apista | |
| | pnomenusa | |
| Pasteurella | multocida | |
| | pneumotrophica | |
| | bettyae | |
| | canis | |
| | dagmatis | |
| | gallinarum | |
| | haemolytica | |
| | stomatis | |
| Pediococcus | acidilactici | |
| | pentosaceus | |
| Peptostreptococcus | magnus | |
| | anaerobius | |
| | micros | |
| | vaginalis | |
| | asaccharolyticus | |
| | tetradius | |
| | prevotii | |
| Photorhabdus | luminescens | |
| | asymbiotica | |
| Plesiomonas (Plesiomonas) | shigelloides | |
| Porphyromonas | gingivalis | |
| | levii | |
| | uenonsis | |
| Prevotella | melaninogenica | |
| | intermedia | |
| | bivia | |
| | heparinolytica | |
| | nigrescens | |
| | oris | |
| | disiens | |
| Propionibacterium | acnes | |
| | propionicus | |
| Proteus | mirabilis | |
| | vulgaris | |
| | penneri | |
| Providencia | alcalifaciens | |
| | rettgeri | |
| | stuartii | |
| Pseudomonas | aeruginosa | |
| | fluorescens | |
| | putida | |
| | mendonica | |
| | alcaligenes | |
| | pickettii | |
| | maltophila | |
| | cepacia | |
| | mallei | |
| | pseudomallei | |
| | oryzihabitans | |
| | stutzeri | |
| | putrefaciens | |
| Ralstonia | picketii | |
| | mannitolilytica | |
| Rhizobium | radiobacter | |
| | massiliae | |
| Rhodococcus | equi | |
| Rickettsia | tsutsugamuchi | |
| | conorii | |
| | prowazekii | |
| | rickettsii | |
| | akari | |
| | japonica | |
| | austral(ens)is | |
| | typhi | |
| | monogolotimonae | |
| | felis | |
| | parkeri | |
| | helvetica | |
| | canada | |
| | montana | |
| | sennetsu | |
| Rochalimaea | quintana | |
| Roseomonas | gilardii | |
| | fauriae | |
| | mucosa | |
| Rothia | dentocariosa | |
| Salmonella | typhi | |
| | arizonae | |
| | enteritidis | |
| | paratyphi | |
| | typhimurium | |
| | enterica | |
| | dublin | |
| | choleraesuis | |
| Selenomonas | sputagena | |
| Serpulina | hyodysenteriae | |
| | pilosicoli | |
| | murdochii | |
| Serratia | marcesans | |
| | liquefaciens | |
| Shigella | flexneri | |
| | boydii | |
| | dysenteriae | |
| | sonnei | |
| Sneathia | sanguinegens | |
| Staphylococcus | aureus | |
| | epidermidis | |
| | saphrophyticus | |
| | lugdunensis | |
| | haemolyticus | |
| | warneri | |

TABLE 1A-continued

Non-exclusive list of Human Bacterial Pathogens

| Genus | Species | Comments |
|---|---|---|
| | schleferi | |
| | intermedius | |
| Stenotrophomonas | maltophilia | |
| Streptobacillus | moniliformis | |
| Steptococcus | pneumoniae | |
| | gordonii | |
| | gallolyticus | |
| | pyogenes | |
| | mutans | |
| | sanguis | |
| | iniae | |
| | agalactiae | |
| | faecalis | |
| | suis | |
| | equisimilis | |
| | bovis | |
| | salivarius | |
| | mitis | |
| | milleri group | |
| | Group A, B, C, D, F, G, R | |
| | A, β, γ type | |
| Streptomyces | somaliensis | |
| Streptophomonas | maltophila | |
| Thermoactinomyces | sacchari | |
| | vulgaris | |
| | dichotomicus | |
| Thermomonospora | viridis | |
| Treponema | carateum | |
| | pallidum | |
| | pertenue | |
| | denticola | |
| Tropheryma | whippelii | |
| Ureaplasma | urealyticum | |
| | parvum | |
| Vagococcus | fluvialis | |
| Veillonella | montpellierensis | |
| | parvula | |
| | alcalescens | |
| Weisella | confusa | |
| | cibaria | |
| Vibrio | cholerae | |
| | parahaemolyticus | |
| | vulnificus | |
| | alginolyticus | |
| | mimicus | |
| | hollisae | |
| | fluvialis | |
| | damsella | |
| | furnisii | |
| | metchnikovii | |
| Yersinia | pestis | |
| | enterocolitica | |
| | pseudotuberculosis | |

TABLE 1B

Non-exclusive list of Human Fungal Pathogens

| Genus | Species | Comments |
|---|---|---|
| Absidia | corymbifera | |
| Acremonium | Falciforme | |
| | kiliensis | |
| | recifei | |
| Apophysomyces | elegans | |
| Ajellomyces | Dermatitidis | |
| | Capsulatus | |
| Alternaria | alternata | |
| Arthroderma | vanbreuseghemii | |
| Arthrographis | kalrae | |
| | Grisea | |
| | cuboidea | |

TABLE 1B-continued

Non-exclusive list of Human Fungal Pathogens

| Genus | Species | Comments |
|---|---|---|
| Aspergillus | Fumigatus | |
| | Ochraceus | |
| | Versicolor | |
| | Flavus | |
| | terreus | |
| | glaucus | |
| | Nidulans | |
| | niger | |
| | Oryzae | |
| | flavatus | |
| | ustus | |
| Basidiobolus | Ranarum | |
| | Meristosporus | |
| | haptosporus | |
| Beauveria | bassiana | |
| Bipolaris | spicifera | |
| | Australiensis | |
| | hawaiiensis | |
| Blastomyces | Dermatitidis | |
| | brasiliensis | |
| Blastoschizomyces | capitatum | |
| Candida | Albicans | |
| | Tropicalis | |
| | Glabrata | |
| | parapsilosis | |
| | krusei | |
| | zeylanoides | |
| | guillermondii | |
| | pelliculosa | |
| | Kefyr | |
| | dubliniensis | |
| Chrysosporium | Keratinophilum | |
| | Tropicum | |
| | Merdarium | |
| | Inops | |
| | Pannicola | |
| | Queenslandicum | |
| | Zonatum | |
| | parvum | |
| Cladophialophora | Bantiana | |
| | carrionii | |
| Cladosporium | Bantianum | |
| | Caldosporiodes | |
| Coccoides | Immitis | |
| Conidiobolus | coronatus | |
| Coniothyrium | fuckelii | |
| Cryptococcus | neoformans | Var neoformans & gattii & grubii |
| | Albidus | |
| | laurentii | |
| Cunninghamella | bertholletiae | |
| Curvularia | Brachyspora | |
| | Clavata | |
| | Geniculata | |
| | Lunata | |
| | Pallescens | |
| | Senegalensis | |
| | verruculosis | |
| Emmonsia | Parva | Var parva & crescens |
| Epidermophyton | Floccosum | |
| | rubrum | |
| | stockdaleae | |
| | gallinae | |
| Exophiala | jeanselmiae | |
| | dermatitidis | |
| Exserohilum | Rostratum | |
| | Halodes | |
| | meginnisii | |
| | longirostratum | |
| Filobasidiella | neoformans | Var neoformans & gattii |
| Fonsecaea | Compacta | |
| | Pedrosoi | |
| Fusarium | oxyporum | |
| | solani | |

TABLE 1B-continued

Non-exclusive list of Human Fungal Pathogens

| Genus | Species | Comments |
|---|---|---|
| Geotrichium | candidum | |
| Histoplasma | Capsulatum | Var *capsulatum, dubiosii* & *farcinimosum* |
| Lacazia | loboi | |
| Lasiodiplodia | theobromae | |
| Leptosphaeria | senegalensis | |
| Loboa | loboi | |
| Madurella | Grisea | |
| | mycetomatis | |
| Malassezia | furfur | |
| Microsporum | gypseum | |
| | Audoinii | |
| | canis | |
| | Nanum | |
| | Fulvum | |
| | ferrugineum | |
| | distortum | |
| Mucor | Ramosissimus | |
| | Indicus | |
| | circinneloides | |
| | hiemalis | |
| Neotestudina | Rosatii | |
| Nocardiopsis | dassonvillei | |
| Ochroconis | gallopava | |
| Onchyocola | canadiensis | |
| Paecilomyces | crustaceus | |
| | variotii | |
| Paracoccidiomyces | brasiliensis | |
| Paracoccidioides | Brasiliensis | |
| Penicillium | Marneffei | |
| | verrucosum | |
| Phaeoannellomyces | werneckii | |
| Phialophora | verrucosa | |
| | Repens | |
| | parasitica | |
| Phoma | Cruris-hominis | |
| Piedaria (Piedra) | Hortae (iahortae) | |
| Pneumocystis | carinii | |
| | Jiroveci(i) | |
| Pseudallescheria | Boydii | |
| Pyrenochaeta | romeroi | |
| Rhinosporidium | seeberi | |
| Rhizomucor | pusillus | |
| Rhizopus | arrhizus | |
| Rhodotorula | Rubra | |
| | Minuta | |
| | Glutinis | |
| | mucilaginosa | |
| Saccharomyces | cerevisiae | |
| | Boulardii | |
| Scedosporium | Apiospermum | |
| | Proliferans | |
| | Inflatum | |
| Scopulariopsis | brevicaulis | |
| Schizophyllum | commune | |
| Scytalidium | Dimidiatum | |
| | hyalinum | |
| Sporobolomyces | salmonicolor | |
| Sporothrix | Schenckii | |
| Stachybotrys | Chartarum | |
| | Atra | |
| | alternans | |
| Synchephalastrum | racemosum | |
| Trichoderma | longibrachiatum | |
| Trichophyton | Rubrum | Including var *nigricans* & *granular* |
| | Interdigitale | |
| | Mentagrophytes | Including var *interdigitale* & *goetzii* |
| | Violaceum | |
| | Tonsurans | |
| | schoenleinii | |
| | Megninii | |
| | concentricum | |
| | Sourdanense | |
| | gourvilii | |
| | verrucosum | |
| | terrestre | |
| Trichosporon | beigleii | |
| Ulocladium | botyris | |
| | chartarum | |
| Ustilago | maydis | |
| Verticillium | affinae | |
| | Albo-atrum | |
| | fusisporum | |
| | luteoalbum | |
| Wangiella | dermatitidis | |
| Xylohypha | Bantiana | |

TABLE 1C

Non-exclusive list of Human Parasitic Pathogens

| Genus | Species | Comments |
|---|---|---|
| Acanthamoeba | castellanii | |
| | culbertsoni | |
| Ancylostoma | duodenale | |
| Angiostrongylus | cantonensis | |
| | costaricensis | |
| Anisakis | simplex | |
| Ascaris | lumbricoides | |
| | suum | |
| Babesia | divergens | |
| | microti | |
| | Equi | |
| Balamuthia | mandrillaris | |
| Balantidium | coli | |
| Blastocystis | hominis | |
| Brugia | malayi | |
| | pahangi | |
| | timori | |
| Capillaria | philipinensis | |
| Clonorchis | sinensis | |
| | viverrini | |
| Contracaecum | osculatum | |
| Cryptosporidium | parvum | |
| Cyclospora | cayetanensis | |
| Dicrocoelium | dendriticum | |
| Dientamoeba | fragilis | |
| Diphyllobothrium | latum | |
| Dirofilaria | immitis | |
| Dracunculus | medinensis | |
| Echinococcus | granulosus | |
| | multilocaris | |
| | vogeli | |
| Entamoeba | histolytica | |
| Enterobius | vermicularis | |
| Enterocytozoon | bieneusi | |
| Fasciola | gigantica | |
| | hepatica | |
| | buski | |
| Giardia | lamblia | |
| | intestinalis | |
| Heterophyes | | |
| Hymenolepis | diminuta | |
| | nana | |
| Isospora | belli | |
| Leishmania | aethipoica | |
| | brasiliensis | |
| | donovani | |
| | mexicana | |
| | peruviana | |
| | major | |
| | tropica | |
| | amazonensis | |
| | panamensis | |
| | guyanensis | |

TABLE 1C-continued

Non-exclusive list of Human Parasitic Pathogens

| Genus | Species | Comments |
|---|---|---|
| | infantum | |
| | chagasi | |
| Loa | loa | |
| Mansonella | ozzardi | |
| | perstans | |
| | streptocerca | |
| Naegleria | fowleri | |
| Necator | americanus | |
| Onchocerca | volvulus | |
| Opisthorcis | felineus | |
| | sinensis | |
| | viverinni | |
| Paragonimus | westermani | |
| Plasmodium | falciparum | |
| | vivax | |
| | Malariae | |
| | ovale | |
| Pneumocystis | carinii | |
| Pseudoterranova | decipiens | |
| Rhinosporidium | seeberi | |
| Sarcocystis | suihominis | |
| Schistosoma | haematobium | |
| | intercalatum | |
| | japonicum | |
| | mansoni | |
| | mekongi | |
| Spirostomum | teres | |
| Strongyloides | stercoralis | |
| Taenia | saginata | |
| | solium | |
| Theileria | parva | |
| Toxocara | canis | |
| | cati | |
| Toxoplasma | gondii | |
| Trichinella | native | |
| | nelsoni | |
| | spiralis | |
| | psuedospiralis | |
| Trichomonas | vaginalis | |
| Trichostrongylus | orientalis | |
| Trichuris | trichiura | |
| Trypanosoma | cruzi | |
| | brucei brucei | |
| | brucei gambiense | |
| | brucei rhodesiense | |
| Wuchereria | bancrofti | |

TABLE 1D

Non-exclusive list of Human Enveloped Viral Pathogens
Enveloped virus: A virus having an outer lipoprotein bi-layer acquired by budding through the host cell membrane.

| Virus | Disease | Comments |
|---|---|---|
| TOGAVIRIDAE | | |
| Alphaviruses: | | |
| Eastern equine encephalomyelitis | Fever, malaise, headaches, encephalitis | |
| Western equine encephalomyelitis | Fever, malaise, headaches, encephalitis | |
| Venezuelan equine encephalomyelitis | Fever, malaise, headaches, encephalitis | Includes Mucambo, Everglades, Tonate, Pixuna, Cabassou virus/fever |
| Ross river | Fever, rash, arthralgia | |
| Chikungunya | Fever, rash, arthralgia, arthritis | |
| Mayaro | Fever, rash, arthralgia | |
| O'nyong'nyong | Fever, rash, arthralgia | |
| Sindbis | Fever, rash, arthralgia | Ockelbo, Karelian & Pogosta fevers |
| Ndumu | | |
| Middleburg | | |
| Bebaru | | |
| Sagiyama | | |
| Sem(i)liki forest | | |
| Getah | | |
| Rubiviridae: | | |
| Rubella | German Measles | |
| Flaviviruses: | | |
| Yellow fever | hepatitis with a hemorrhagic diathesis | high fever, chills, headache, muscle aches, vomiting, and backache, shock, bleeding, and kidney & liver failure |
| Dengue (types 1, 2, 3 & 4) | immunopathologic disease (shock & haemorrhage) | Dengue fever or Dengue hemorrhagic fever |
| St Louis Encephalitis | encephalitis | |
| Japanese Encapalitis | Encephalitis | |
| Murray Valley Encephalitis | Encephalitis | |
| Russian Spring Summer Encephalitis | Encephalitis | Tick-borne |
| Tick-borne encephalitis | Encephalitis | |
| Kyanasur forest disease | encephalitis | Tick-borne |
| Powassan | Hemorrhagic fever | Tick-borne |
| Hepatitis C | | |
| Hepatitis G | | |
| Israel Turkey Meningitis | Meningitis | |
| Rocio | | |
| Sal Vieja | | |
| San Perlita | | |
| Spondweni | | |
| Wesselsbron | | |
| West Nile Fever | | |
| Absettarov | | Tick-borne |
| Hanzalova | | Tick-borne |
| Hypr | | Tick-borne |
| Kumlinge | | Tick-borne |
| Louping ill | | Tick-borne |
| Negishi | | Tick-borne |
| Omsk | | Tick-borne |
| BUNYAVIRIDAE | | |
| Bangui | Fever, rash | |
| Bhanja | Fever, encephalitis | |
| Issk-kul | Fever | |
| Kasokero | Fever | |
| Nyando | Fever | |
| Tamdy | Fever | |
| Tataguine | Fever | |
| Wanowrie | Fever, hemorrhage | |
| Bunyaviruses: | | |
| Akabene | | |
| Bunyamwera | Fever | Bunyamwera, Germiston, Ilesha, Shokwe, Tensaw, Wyeomyia |
| Bwamba | Fever | Bwamba, Pongola |

TABLE 1D-continued

Non-exclusive list of Human Enveloped Viral Pathogens
Enveloped virus: A virus having an outer lipoprotein bi-layer acquired by budding through the host cell membrane.

| Virus | Disease | Comments |
|---|---|---|
| C | Fever | Apeu, Caraparu, Itaqui, Madrid, Marituba, Murutucu, Nepuyo, Oriboca, Ossa, Restan |
| California | Fever &/or Encephalitis | California encephalitis, Guaroa, Inkoo, La Crosse, Snowshoe hare, Jamestown Canyon, Tahyna |
| Guama | Fever | Catu, Guama |
| Simbu | Fever | Shuni, Oropouche |
| Phleboviridae: | | |
| Phlebotomous fever | fever | Alenquer, Candinu, Chagres, Naples, Punto Toro, Rift Valley Fever, Sicilian, Toscana |
| Sandfly fever | | |
| Nairoviridae: | | |
| Crimean-Congo | Hemmorhagic fever | |
| Nairobi Sheep Disease | Fever | |
| Hazara | | |
| Hantaviridae: | | |
| Hantaan | Hemorrhagic fever with renal syndrome or Hantavirus Pulmonary Syndrome | Hantaan (Korean haemorrhagic fever), Puumala, Seoul, Sin Nombre (Muerto Canyon), New York, Black Creek Canal |
| Belgrade (Dobrava) | | |
| Prospect Hill | | |
| ARENAVIRIDAE | | |
| LCM-Lassa-virus-complex (Old World Arenaviruses) | | Ippy, Lassa Fever, Lymphotic choriomeningitis, Mobala, Mobeia |
| Tacaribe-virus-complex | | Ampari, Flexal, Guanarito, Junin, Latino, Machupo, Parana, Pichinde, Sabia, Tamiami |
| ORTHOMYXOVIRIDAE | | |
| Influenza | | Types A, B & C |
| Dhori | | Tick-borne |
| Thogoto | | Tick-borne |
| PARAMYXOVIRIDAE | | |
| Rubulavirus | | Newcastle Disease |
| Nipah | | |
| Hendra | | Equine morbillivirus |
| Human metapneumonovirus | | |
| Paramyxovirus: | | |
| Mumps | | |
| Parainfluenza | mild, febrile common cold to severe, potentially life-threatening croup, bronchiolitis, and pneumonia | Types 1-4 (4 is subdivided into A & B) |
| Pneumovirus: | | |
| Respiratory Synctial Virus | | Types A & B |
| Morbillivirus: | | |
| Measles | | |
| CORONAVIRIDAE | | |
| Coronavirus | Cold | |
| SARS | Severe acute respiratory syndrome | |
| RHABDOVIRIDAE | | |
| Piry | | |
| Lyssaviridae: | | |
| Rabies | Rabies | |
| Lagos Bat | | |
| Mogola | | |
| Duvenhage | | |
| European Bat Lyssavirus | | |
| Vesiculovirus: | | |
| Vesiculovirus | Vesicular Stomatitis | Types 1-4 |
| RETROVIRIDAE | | |
| Oncoviridae: | | |
| Human T-cell Leukaemia | lymphoproliferative and neurologic disorders | Types 1, 2 & 5 |
| Kaposi's sarcoma-associated herpesvirus | | |
| Lentiviridae: | | |
| Human Immunodeficiency Virus | AIDS | Types 1 & 2 |
| Simian Immunodeficiency Virus | | |
| Spumaviridae: | | |
| Human Foamy Virus | | |
| HERPESVIRIDAE | | |
| Herpes simplex | Genital & oral herpes | Types 1 & 2 |
| Varicella-zoster virus | Chicken Pox | |
| Cytomegalovirus | hepatosplenomegaly, retinitis, rash, and central nervous system involvement & possibly mononucleosis | |
| Epstein-Barr virus | Mononucleosis | |
| Human herpesvirus | exanthem subitem (roseola) | Types 6 & 7 |
| Kaposi's Sarcoma virus | Kaposi's sarcoma | Human herpesvirus type 8 |
| B virus | encephalitis | |
| FILOVIRIDAE | | |
| Ebola Reston | multiple hemorrhagic manifestations, marked hepatic involvement, disseminated intravascular coagulation, and shock | |

TABLE 1D-continued

Non-exclusive list of Human Enveloped Viral Pathogens
Enveloped virus: A virus having an outer lipoprotein bi-layer acquired by budding through the host cell membrane.

| Virus | Disease | Comments |
| --- | --- | --- |
| Ebola Siena | | |
| Ebola Sudan | | |
| Ebola Zaire | | |
| Marburg | | |

Thus the invention provides the use of a peptide according to the invention in the manufacture of a medicament for treating a microbial infection wherein the microbial infection is a systemic, topical, subcutaneous, cutaneous or mucosal fungal infection.

Fungal infections can be classified as systemic, meaning that the infection is deep and affects internal organs, blood borne, or topical (dermatophytic), meaning that the infection is superficial and occurs on the skin. Additionally, yeast infections can affect the mucous membranes of the body. Yeast infections can also be systemic (e.g. candidaemia and other frequently fatal conditions). Fungal infections on the skin are usually treated with creams or ointments (topical antifungal drugs). However, systemic infections, yeast infections or topical infections that do not clear up after treatment with creams or ointments may need to be treated with systemic antifungal drugs (oral or IV). These drugs are used, for example, to treat common fungal infections such as tinea (ringworm), which occurs on the skin or candidiasis (a yeast infection, also known as thrush), which can occur in the throat, in the vagina, or in other parts of the body. Systemic antifungal drugs are also used to treat other deep fungal infections such as histoplasmosis, blastomycosis, and aspergillosis, which can affect the lungs and other organs. They are sometimes used to prevent or treat fungal infections in people whose immune systems are weakened, such as bone marrow or organ transplant patients and people with HIV-AIDS.

Topical or dermatophytic fungal infections, while not typically causative of death or of serious illness, are prevalent and are economically important because they can be expensive to treat. Topical or superficial fungal infections may include those of the skin, lamina, stratum corneum, nails and hair. Cutaneous infections are infections of the skin, finger nails and toenails.

In a preferred aspect of the invention, the fungal infection is onychomycosis. Onychomycosis may be caused by a fungus from, but not limited to, the genus *Trichophyton* spp., for example, the fungus may be *Trichophyton interdigitale* or *Trichophyton rubrum*.

The term "onychomycosis" includes, but is not limited to, distal lateral subungual, superficial white, proximal white subungual, secondary dystrophic, primary dystrophic, endonyx, candidal (e.g. onycholysis & chronic mucocutaneous disease) types of onychomycosis. Onychomycosis has been shown as a significant risk factor for more serious clinical complications, such as acute bacterial cellulitis of the arm/leg and other secondary bacterial infections, thus the present invention encompasses the treatment of these infections.

The peptides of the invention are potent antimicrobial peptides for a wide variety of pathogenic organisms. However, the peptides of the invention may also be useful in the treatment of other conditions including, but not limited to, cystic fibrosis and other conditions associated with mucosal infections, for example, gastrointestinal, urogenital or respiratory infections.

The peptides of the invention may also be useful in the treatment or prevention of, inter alia, wounds, ulcers and lesions for example, cutaneous wounds such cuts or burns, and conditions associated therewith.

The term "treatment" relates to the effects of the peptides described herein that in imparting a benefit to patients afflicted with an (infectious) disease, including an improvement in the condition of the patient or delay in disease progression.

As used herein "treatment of a wound" may include wound healing and associated conditions and therapy which promotes, augments, or accelerates healing of tissues and includes post-operative scarring, burns, psoriasis, acceleration of tissue remodelling, for example, post cosmetic surgery and organ transplantation.

Thus, in a further aspect of the invention there is provided a substrate to which a peptide of the invention is applied or attached. Preferably, the substrate is suitable for application to wounds or delivery to wound sites. Preferably, the substrate allows for the transfer of the peptides of the invention from the substrate to a wound bed to achieve their antibiotic effect. The substrate may be a dressing, for example, wound dressing. The dressing may comprise a fabric material or it may be a collagen-like material.

The peptides of the invention may also find application as/in a disinfectant. In this context, the peptide or pharmaceutical compositions of the invention may be applied, either alone or in combination with other disinfecting agents, to a surface to be treated. As used herein a "surface to be treated" may be a substrate as defined herein or a medical device.

In a further aspect, the invention provides a method of treating or preventing a microbial infection in a subject comprising administering to said subject a therapeutically effective amount of a peptide according to the invention.

In a preferred method of the invention, the microbial infection is a fungal infection. In the method of the invention the peptide may be applied to the skin or nails of said subject.

Mammals, birds and other animals may be treated by the peptides, compositions or methods described herein. Such mammals and birds include humans, dogs, cats and livestock, such as horses, cattle, sheep, goats, chickens and turkeys and the like. Moreover, plants may also be treated by the peptides, compositions or methods of the invention.

Where the subject is an animal, the method of the invention may be applied to nail-like features, including, but not exclusive to, hooves, claws and trotters.

The method of the invention may include, in addition to peptide treatment, treatments that may enhance peptide permeation into the nail. This could be facilitated by chemical or physical means. Physical treatments, such as nail etching or filing of the dorsal layer of the nail may enhance permeability of the peptides of the invention. Chemical enhancement of nail permeability to the peptides of the invention may be achieved by breaking physical or chemical bonds within the nail plate keratin. Nail softening agents, including, but not exclusive to, urea and salicylic acid, increase hydration of the nail to decrease nail density and, therefore, may increase permeability to the peptides of the invention. Compounds containing sulfhydryl groups will cleave the disulphide bonds in nail keratin, and may lead to destabilization and increased permeability of drugs. Compounds including, but not exclusive to acetylcysteine and mercaptoethanol derivatives may be used in combination with our peptides. Other known nail permeability excipients/adjuvants that may be used in combination with the peptides of the invention include methylsulfonylmethane, urea, polyethylene glycol, N-(-2-mercaptopropionyl)glycine, dimethylsulfone and 2-n-nonyl-1,3-dioxolane.

In a further aspect, the invention provides a method of treating a wound in a subject comprising applying to the wound a therapeutically effective amount of a peptide, or a substrate, according to the invention.

The peptides of the invention, including their salts, are administered so as to achieve a reduction in at least one symptom associated with an infection, indication or disease, or a decrease in the amount of antibody associated with the indication or disease.

To achieve the desired effect(s), the peptide, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results. The amount administered will vary depending on various factors including, but not limited to, the peptide chosen and its clinical effects, the disease, the weight, the physical condition, the health, the age of the mammal, whether prevention or treatment is to be achieved, and if the peptide is chemically modified. Such factors can be readily determined by the clinician examining the empirical data from the clinical trials and examining the preclinical animal model results or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the peptides of the invention may be essentially continuous over a pre-selected period of time or may be in a series of spaced doses. Both local and systemic administration is contemplated.

To prepare the composition, peptides are synthesized or otherwise obtained, purified as necessary or desired, and then lyophilized and stabilized. The peptide can then be adjusted to the appropriate concentration and optionally combined with other agents. The absolute weight of a given peptide included in a unit dose can vary widely. For example, about 0.01 to about 2 g or about 0.01 to about 500 mg, of at least one peptide of the invention, or a plurality of peptides specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the peptides of the invention can vary as well. Such daily doses can range, for example, from about 0.001 g/day to about 100 or 50 g/day, from about 0.1 g/day to about 25 g/day, from about 0.1 g/day to about 12 g/day, from about 0.1 g/day to about 5 g/day, from about 0.1 g/day to about 2.5 g/day, from about 0.1 g/day to about 2 g/day, from about 0.5 g/day to about 8 g/day, from about 0.5 g/day to about 4 g/day, from about 0.5 g/day to about 2 g/day, and from about 0.5 g/day to about 1 g/day.

Thus, one or more suitable unit dosage forms comprising the therapeutic peptides of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic peptides may also be formulated in a lipid formulation or for sustained release (for example, using microencapsulation, see WO 94/07529, and U.S. Pat. No. 4,962,091). The formulations may, where appropriate, be conveniently presented in discrete unit dosage forms and may be prepared by any of the methods well-known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic peptides of the invention are prepared for oral administration, they are generally combined with a pharmaceutically acceptable carrier, diluent or excipient to form a pharmaceutical formulation, or unit dosage form. For oral administration, the peptides may be present as a powder, a granular formation, a solution, a suspension, an emulsion or in a natural or synthetic polymer or resin for ingestion of the active ingredients from a chewing gum. The active peptides may also be presented as a bolus, electuary or paste. Orally administered therapeutic peptides of the invention can also be formulated for sustained release, e.g., the peptides can be coated, micro-encapsulated, or otherwise placed within a sustained delivery device. The total active ingredients in such formulations comprise from 0.1 to 99.9% by weight of the formulation.

Pharmaceutical formulations containing the therapeutic peptides of the invention can be prepared by procedures known in the art using well-known and readily available ingredients. For example, the peptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatine, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the peptides of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinized starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like.

Hard or soft gelatin capsules containing at least one peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more peptides of the invention are designed to resist disintegration in the stomach and dissolve in the more neutral to alkaline environment of the duodenum.

The therapeutic peptides of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic peptides of the invention can also take the form of an aqueous or anhydrous solution or dispersion, or alternatively the form of an emulsion or suspension or salve.

Thus, the therapeutic peptides may be formulated for parenteral administration (e.g. by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active peptides and other ingredients may form suspensions, solutions, or emulsions in oily or aqueous vehicles, and may contain formulatory agents such as suspending, stabilizing and/or dispersing agents. Alternatively, the active peptides and other ingredients may be in powder form, obtained by aseptic isolation of sterile solid or by lyophilization from solution for constitution with a suitable vehicle, e.g., sterile, pyrogen-free water before use.

These formulations can contain pharmaceutically acceptable carriers, vehicles and adjuvants that are well-known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulfoxide, glycol ethers such as the products sold under the name "Dowanol", polyglycols and polyethylene glycols, $C_1$-$C_4$ alkyl esters of short-chain acids, ethyl or isopropyl lactate, fatty acid triglycerides such as the products marketed under the name "Miglyol", isopropyl mytrisate, animal, mineral and vegetable oils and polysiloxanes.

Preferably, the pharmaceutical formulations of the therapeutic peptides of the invention can also take the form of a solvent or diluent comprising the peptide. Solvents or diluents may include acid solutions, dimethylsulphone, N-(2-mercaptopropionyl) glycine, 2-n-nonyl-1,3-dioxolane and ethyl alcohol. Preferably the solvent/diluent is an acidic solvent, for example, acetic acid, citric acid, boric acid, lactic acid, propionic acid, phosphoric acid, benzoic acid, butyric acid, malic acid, malonic acid, oxalic acid, succinic acid or tartaric acid.

More preferably, the solvent is an acetic acid solution. The solvent, for example acetic acid solution, may be present in the composition at a concentration of less than 1%, 0.5%, 0.25%, 0.1%, 0.05% or 0.01% acid.

In a further aspect of the present invention there is provided the use of an acid in the manufacture of a medicament for treating a microbial infection, in particular a fungal infection. The fungal infection may be onychomycosis. Onychomycosis may be caused by a fungus from, but not limited to the genus *Trichophyton* spp., for example, the fungus may be *Trichophyton interdigitale* or *Trichophyton rubrum*. The acid may be as hereinbefore described. Preferably the acid is acetic acid. Preferably still the acid is provided in solution at a concentration of less than 1%, 0.5%, 0.25%, 0.1%, 0.05% or 0.01% acid, for example acetic acid. Typically the medicament is adapted for topical administration for treatment of, for example, nails.

As used hereinafter, the term "active agent" encompasses a single peptide according to the invention, or a combination of peptides as described herein. The term "active agent" may also encompass a pharmaceutically effective amount of an acid as herein described. The active agents may be administered simultaneously, sequentially or separately. It is generally preferred that such administration be topical.

The active agents may be administered in synergistically effective amounts. The invention therefore includes: the use of synergistically effective amounts of the active agents, for example a peptide according to the invention and a pharmaceutically effective amount of an acid as herein described, for the manufacture of a product, e.g. a medicament, for simultaneous, separate or sequential administration of said agents in the treatment of a microbial infection.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivates can be added.

Also contemplated are combination products that include one or more peptides of the present invention and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that the peptides might be combined with topical antifungal agents such as ciclopirox olamine, haloprogin, tolnaftate, undecylenate, topical nysatin, amorolfine, butenafine, naftifine, terbinafine, and other topical agents.

Additionally, the peptides are well suited to formulation as sustained release dosage forms and the like. The formulations can be so constituted that they release the active peptide, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

For topical administration, the active agents may be formulated as is known in the art for direct application to a target area. Forms chiefly conditioned for topical application take the form, for example, of creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration. Alternatively, the peptide can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Topical administration may be in the form of a nail coating or lacquer. For example, the antifungal peptides can be formulated in a solution for topical administration that contains ethyle acetate (NF), isopropyl alcohol (USP), and butyl monoester of poly[methylvinyl ether/maleic acid] in isopropyl alcohol.

Pharmaceutical formulations for topical administration may comprise, for example, a physiologically acceptable buffered saline solution containing between about 0.001 mg/ml and about 100 mg/ml, for example between 0.1 mg/ml and 10 mg/ml, of one or more of the peptides of the present invention specific for the indication or disease to be treated.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active peptides can also be delivered via iontophoresis, e.g., as disclosed in U.S. Pat. No. 4,140,122; 4,383,529; or 4,051,842. The percentage by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic peptides in an aqueous or non-aqueous base also comprising one or more dispersing agents, solubilizing agents or suspending agents. Liquid sprays can be pumped, or are conveniently delivered from pressurized packs. Drops can be delivered via a simple eye dropper-capped bottle, via a plastic bottle adapted to deliver liquid contents drop-wise, or via a specially shaped closure.

The therapeutic peptide may further be formulated for topical administration in the mouth or throat. For example, the active ingredients may be formulated as a lozenge further comprising a flavored base, usually sucrose and acacia or tragacanth; pastilles comprising the composition in an inert base such as gelatine and glycerine or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The peptides of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g. gelatine or blister packs from which the powder may be administered with the aid of an inhalator, insufflator, or a metered-dose inhaler (see, for example, the pressurized metered dose inhaler (MDI) and the dry powder inhaler disclosed in Newinan, S. P. in *Aerosols and the Lung*, Clarke, S. W. and Davia, D. eds., pp. 197-224, Butterworths, London, England, 1984).

Therapeutic peptides of the present invention can also be administered in an aqueous solution when administered in an aerosol or inhaled form. Thus, other aerosol pharmaceutical formulations may comprise, for example, a physiologically acceptable buffered saline solution containing between about 0.001 mg/ml and about 100 mg/ml of one or more of the peptides of the present invention specific for the indication or disease to be treated. Dry aerosol in the form of finely divided solid peptide or nucleic acid particles that are not dissolved or suspended in a liquid are also useful in the practice of the present invention. Peptides of the present invention may be formulated as dusting powders and comprise finely divided particles having an average particle size of between about 1 and 5 µm, alternatively between 2 and 3 µm. Finely divided particles may be prepared by pulverization and screen filtration using techniques well-known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic peptides of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention also provides a screening assay for peptides that have low toxicity for normal human or other animal cells but have desirable antimicrobial, e.g. antifungal, properties (permeabilizing fungal cell membranes, lysing or otherwise killing or inhibiting the growth of fungi).

Candidate peptides may be obtained from libraries of the peptides of the invention as described herein. The peptides can also be individually or rationally designed to have specific structural features.

BRIEF DESCRIPTION OF THE DRAWINGS

The invention will now be described by way of Example only with reference to the following figures wherein:

FIG. 1 shows the amino acid sequences of four peptides according to the invention (SEQ ID NO: 7-10, referred to as Peptides 1-4, respectively);

DETAILED DESCRIPTION

Figure 2:
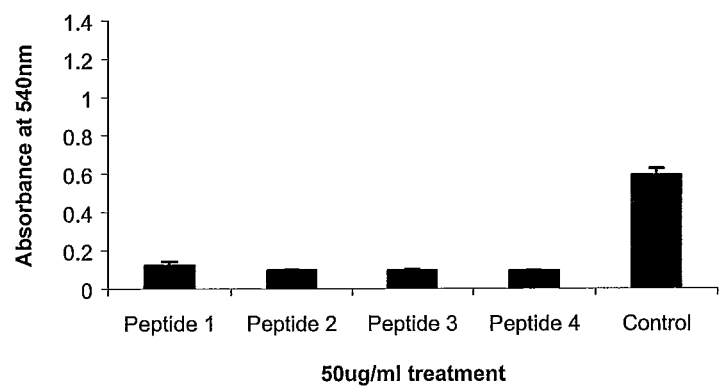
FIG. 2 is a histogram demonstrating the growth of the fungus, *T. interdigitale* after (a) 4 days and (b) 7 days of treatment with the peptides of FIG. 1.
Figure 2:
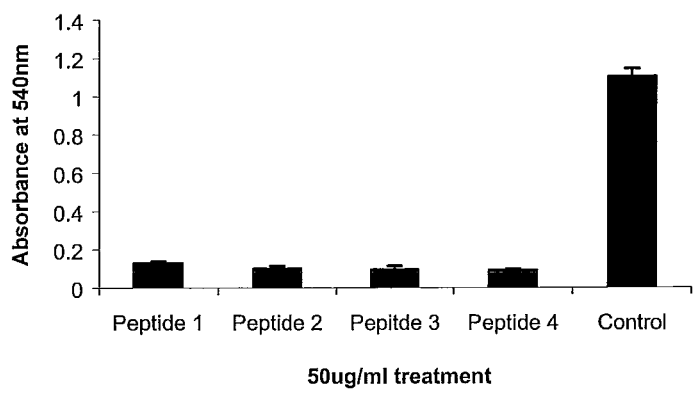

The invention will now be described by way of reference only to the following examples.

EXAMPLES

Materials and Methods

All peptides were produced either by solid-phase synthesis under contract by Invitrogen-Evoquest, Carlsbad, Calif., USA or were obtained from a peptide supplier NeoMPS SA (Strasbourg, France) or Sigma-Aldrich Chemical Company Ltd. (Poole, UK). For tests with fungi, lyophilized peptide was prepared as a stock solution of 1,000 µg/ml in assay buffer. Where explicitly stated in experiments from which FIGS. 2-8 and FIG. 11 were generated, acetic acid was added as a solvent to a final concentration of 0.5%.

Pathogens

*Trichophyton interdigitale* (NCPF 117) and *Trichophyton rubrum* (NCPF 335) strains were obtained from the National Collection of Pathogenic Fungi, Bristol and maintained in culture by transfer at approximately monthly intervals on slopes of Sabouraud's agar and Potato Dextrose Agar at 30° C. *Candida albicans* strain 3179 (obtained from the National Collection of Type Cultures [NCTC], Colindale) was maintained in Oxoid Mueller Hinton Broth at 37° C. *Streptococcus pyogenes* strain 8198, *Staphylococcus aureus* strain 10642 (methicillin-resistant), and *E. coli* 0157 strain 12900 were obtained from the NCTC, Colindale and maintained in Oxoid Mueller Hinton Broth at 37° C.

Fungal Growth Sensitivity Assays

To determine the sensitivity of fungal strains to each of the test peptides, their impact on fungal growth was assessed as follows. Suspensions of *T. interdigitale* and *T. rubrum* conidia and hyphal fragments were prepared by adding 10 ml of fresh Nutrient Glucose Broth (NGB) (Oxoid Nutrient broth containing 2% w/v glucose) to a slope culture and agitating with a spatula. The resulting conidial/hyphal fragment suspension was filtered through 2 layers of sterile surgical gauze to remove large hyphal mats and pieces of agar. 20 µl of this suspension (absorbance at 540 nm around 0.1, corresponding to approx $10^6$ propagules/ml) was inoculated into each well of sterile, 96 well microtitre plates to which a total volume 80 µl of nutrient medium (NGB) and the appropriate amount of peptide solution had previously been added. Control wells were those in which the final assay volume of 100 µl was made up with NGB medium alone, plus solvent (if applicable and at the same concentration as the peptide samples if so). Fungal growth within the plates was monitored by absorbance at 540 nm in a Microtek plate reader after 24 h, 4 day and 7 day incubations at 30° C.

*Candida albicans* Survival Assays

To determine the sensitivity of fungal strains to each of the test peptides, their impact on *Candida* survival was assessed as follows. *C. albicans* cultures were grown for 18-24 h then stored at 4° C. prior to use. Fresh cultures grown overnight were centrifuged at 2000×g for 10 min and washed with fresh Mueller Hinton Broth, adjusting the number of viable cells to between $5 \times 10^6$ and $1 \times 10^7$/ml. Assay buffer was prepared by adding 100 µl of NGB medium to 6.9 ml of 10 mM sodium phosphate buffer, pH 7.7. 35 µl of assay buffer with or without a range of peptide concentrations was added to a sterile polypropylene screw-capped vial and 15 µl of the *Candida albicans* inoculum described above was added. The vials were incubated at 37° C. in a water bath for 2 h, and the number of *Candida* spp. surviving was determined by serial dilution in sterile phosphate buffered saline (PBS) and plating out onto 9 cm Petri dishes containing Oxoid Sabouraud's Agar (20 ml). Counts were made after incubation of these plates at 37° C. for 18-24 h.

Bacterial Survival Assays

Streptococcus pyogenes strain 8198, Staphylococcus aureus strain 10642 (methicillin-resistant), and E. coli O157 strain 12900 (all obtained from the NCTC, Colindale) were grown for 18-24 h then stored at 4° C. prior to use. Fresh cultures grown overnight were centrifuged at 2000×g for 10 min and washed with fresh Mueller Hinton Broth. Sensitivity to each of the four peptides was assayed as per C. albicans described above. For E. coli and S. aureus, the starting number of cells for the peptide sensitivity assay was $10^8$/ml and the medium used for enumeration was Nutrient Agar (Oxoid). Str. pyogenes grew less well than the other strains on Mueller Hinton agar and so the starting number of cells for these assays was lower than that for the other strains, at $10^6$/ml. Str. pyogenes survival was determined using Oxoid Tryptose Soya Agar in place of Nutrient Agar.

Results

Table 2, below, details the peptides which correspond to the amino acid polymer codes shown in the Results and Figures.

TABLE 2

Amino acid polymer codes

KKK - L-Lysine trimer
RRR - L-Arginine trimer
HHH - L-Histidine trimer
WWW - L-Tryptophan trimer
pK3-14 - Poly-L-lysine-HBr 500-2,000Da (3-14aa)
pK7-27 - Poly-L-lysine-HBr 1,000-4,000Da (7-27aa)
pK100-200 - Poly-L-lysine-HCl 15,000-30,000Da (100-200aa)
pKd27-100 - Poly-D-lysine-HBr 4,000-15,000Da (27-100aa)
pR28-86 - Poly-L-arginine-HCl 5,000-15,000 (28-86aa)

Inhibition of Trichophtvon spp. Growth by Peptides 1-4

Two clinically relevant dermal fungal pathogens, Trichopyton rubrum and Trichopyton interdigitale, were cultured, as described previously in the materials and methods section, in growth medium alone (control cultures) or in growth medium containing 50 μg/ml of peptide 1, 2, 3 or 4 (SEQ ID NO: 7-10, respectively; shown in FIG. 1). Growth of T. interdigitale and T. rubrum was assessed by measuring the optical density (absorbance at 540 nm) after 4 and 7 days in culture. Compared to control, un-treated samples, each peptide tested significantly inhibited T. interdigitale (FIG. 2) and T. rubrum (FIG. 3) growth at day 4 and 7. Control cultures of each test strain continued to grow, as indicated by increases in OD readings, between days 4 and 7.

Inhibition of Candida spp. Growth and Survival by Peptides 1-4

Figure 5:
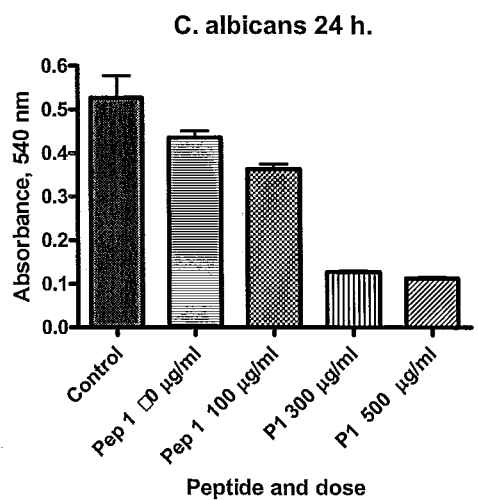
FIG. 5 is a histogram showing the results of a dose-response experiment for peptide 1 (shown in FIG. 1) on the growth of *Candida albicans* after a 24 hour treatment.
Figure 6:
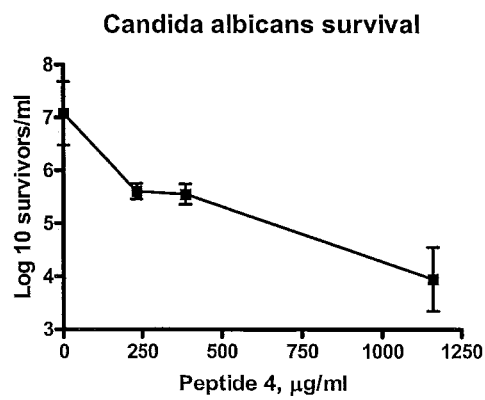
FIG. 6 is a graph showing *Candida* spp. survival at 24 hours in the presence of a range of doses of peptide 4 as shown in FIG. 1.
Figure 7:
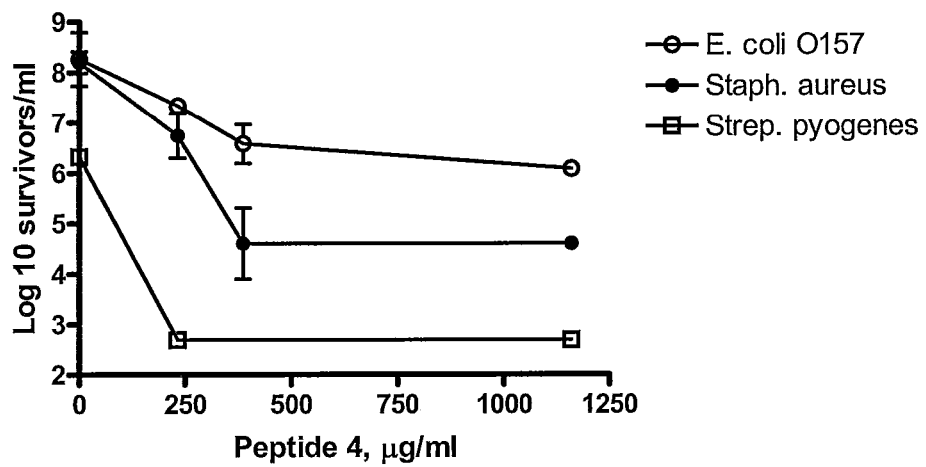
FIG. 7 is a graph showing the survival of 3 different strains of bacteria at 24 hours in the presence of a range of doses of peptide 4 as shown in FIG. 1.
Figure 8:
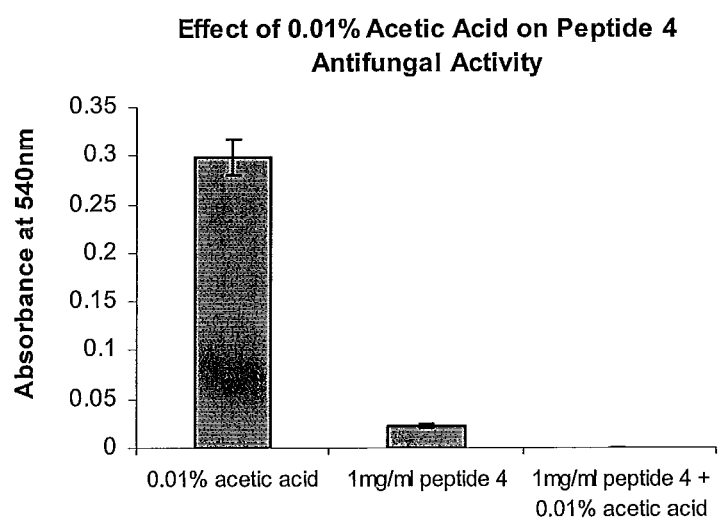
FIG. 8 is a histogram demonstrating the synergistic impact of 0.01% acetic acid on the antifungal activity (against *T. rubrum*) of peptide 4 (1 mg/ml) at day 3 of growth.

The yeast Candida albicans was cultured, as described previously in the materials and methods section, in growth medium alone (control cultures) or in growth medium containing 50 μg/ml or 100 μg/ml and 300 μg/ml or 500 μg/ml of peptide 1, 2, 3 or 4. Growth of C. albicans was assessed by measuring optical density (absorbance at 540 nm) after 24 h (FIG. 4a) and 48 h (FIG. 4b) in culture. Compared to control, un-treated samples, each peptide tested significantly inhibited C. albicans growth in both a time and dose-dependent fashion. Dose-dependency of growth inhibition was further confirmed in experiments in which C. albicans growth was assessed optically after 24 h in culture under control (growth medium alone) conditions or in the presence of a range of concentrations of peptide 1, from 50 μg/ml to 500 μg/ml (FIG. 5). In a separate experiment, C. albicans survival was assessed after 18-24 h in cultures grown in medium alone (controls) or those including a range of concentrations of peptide 4 spanning 1 μg/ml to 1000 μg/ml (FIG. 6). Survival of the C. albicans organisms, as assessed by viability counts after 24 h in culture, decreased in a dose-dependent manner (FIG. 6).

Inhibition of Bacterial Survival by Peptide 4

Three clinically relevant bacterial pathogens, E. coli O157, methicillin-resistant Staphylococcus aureus (MRSA) and Streptococcus pyogenes, were exposed, as described previously in the materials and methods section, to a range of concentrations of peptide 4. After a period of 3 h, samples of each bacterial culture were transferred to appropriate solid phase growth media plates and the numbers of viable colonies in control (growth medium only) and treated (growth medium containing peptide 4) samples assessed after 18-24 h. After 3 h of exposure, Peptide 4 significantly inhibited survival of each bacterial strain (FIG. 7) compared to control, untreated cultures, in a dose dependent manner.

Acetic Acid Enhances Antifungal Activity of Peptide 4

Figure 3:
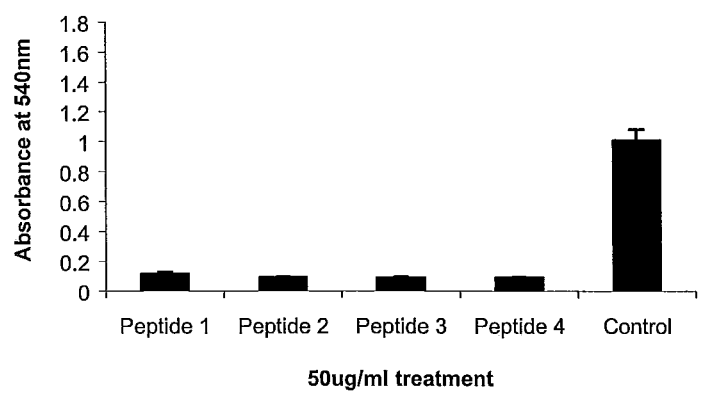
FIG. 3 is a histogram demonstrating the growth of the fungus, *T. rubrum* after (a) 4 days and (b) 7 days of treatment with the peptides of FIG. 1.
Figure 3:
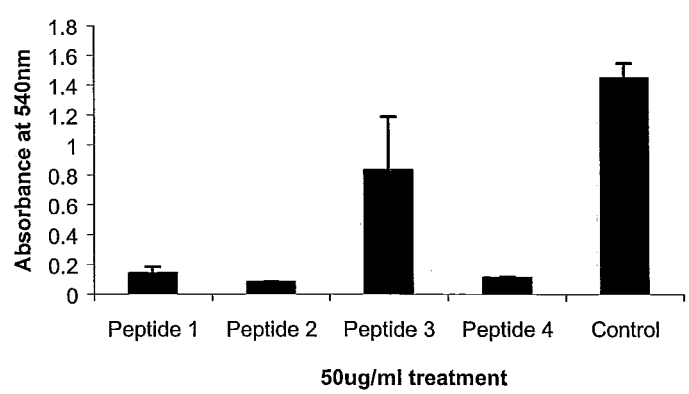
Figure 4:
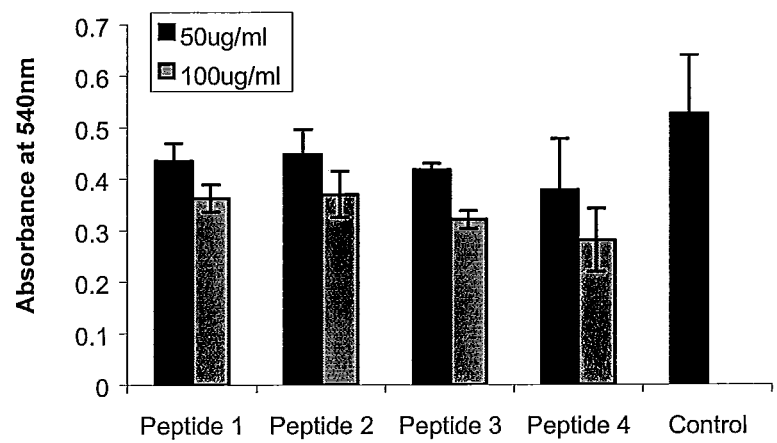
FIG. 4 is a histogram demonstrating the growth of the fungus, *Candida albicans*, after (a) 24 hours and (b) 48 hours of treatment with the peptides of FIG. 1.
Figure 4:
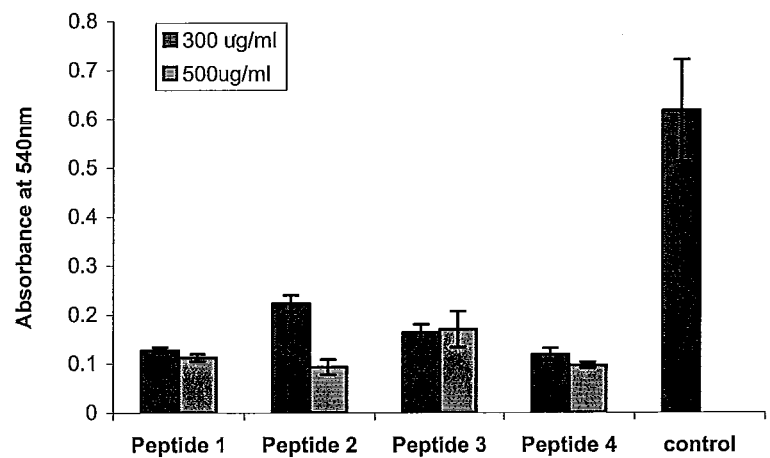

As both control (non peptide) and test (containing peptide 1, 2, 3 or 4) media in experiments shown in FIGS. 2 and 3 contained 0.5% acetic acid as a peptide solvent (detailed in materials and methods section), a separate experiment was set up to ascertain whether the acetic acid itself might play a role in peptide activity and/or fungal survival. To this end, T. rubrum growth experiments were established as per methods and materials section, with growth medium only, growth medium containing only 0.01% acetic acid, growth medium containing 1 mg/ml peptide 4 and growth medium containing 1 mg/ml peptide 4 plus 0.01% acetic acid. Growth of the fungus was determined by OD as described previously after 3 days in culture. As expected, peptide 4 inhibited T. rubrum growth. 0.01% acetic acid alone had no significant effect on T. rubrum growth (FIG. 8), but when included in the medium with peptide 4, the presence of 0.01% acetic acid significantly inhibited T. rubrum growth more than 1 mg/ml of peptide 4 alone.

Inhibition of T. interdigitale and T. rubrum Growth by Peptide 4

Figure 9:
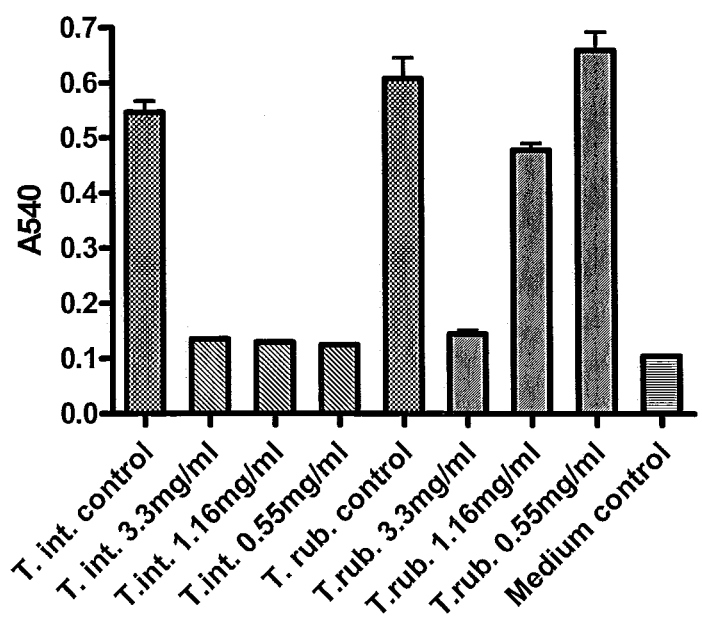
FIG. 9 is a histogram demonstrating the inhibition of *T. interdigitale* and *T. rubrum* by peptide 4.

The inhibitory effects of Peptide 4 on the growth of Trychophyton spp. was determined by fungal growth assay as per materials and methods. T. rubrum and T. interdigitale were cultured in medium alone or in medium containing 3 different concentrations of Peptide 4. No acetic acid was present in any samples. Medium only controls were used to illustrate background absorbance of the media. Growth of the fungus was determined by the OD as described previously after 96 hours of incubation at 30° C. As shown in FIG. 9, these assays confirmed the inhibitory effect of Peptide 4 on the growth of both species of fungi, with T. interdigitale consistently more susceptible to the inhibitory effects of Peptide 4 treatment than T. rubrum. Growth of T. interdigitale was inhibited at peptide concentrations of 0.55 mg/ml.

Effects of Peptides 3 and 4 on T. interdigitale Growth

Figure 10:
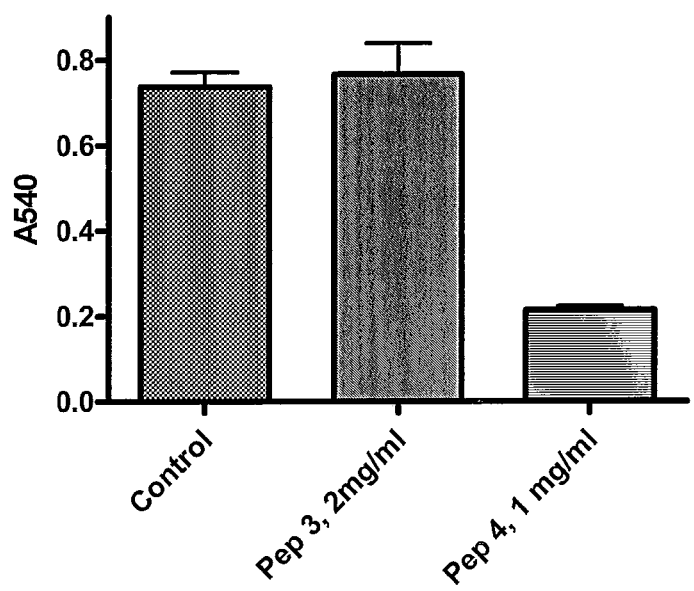
FIG. 10 is a histogram showing the effects of Peptide 3 and 4 on *T. interdigitale;*

The antifungal potential of Peptide 3 and Peptide 4 on T. interdigitale was assessed. Growth inhibition assays were performed as per materials and methods in the absence of acetic acid. As Peptides 1-3 are highly hydrophobic and therefore insoluble they had only previously been tested against Trichophyton spp. in acetic acid as solvent. When T. interdigitale cultures were grown for 7 days in the presence of Peptide 3, Peptide 4 or medium alone with no acetic acid solvent and growth measured by OD, Peptide 4 was seen to significantly inhibit fungal growth (FIG. 10), whereas Peptide 3 showed no inhibitory activity (FIG. 10). This increased activity of the cationic Peptide 4 over the hydrophobic Peptide 3 in the absence of 0.5% acetic acid suggested a significant contribution of the acetic acid to the activity seen for the hydrophobic peptides previously.

Effect of Acetic Acid on the Growth of *T. interdigitale*

Figure 11:
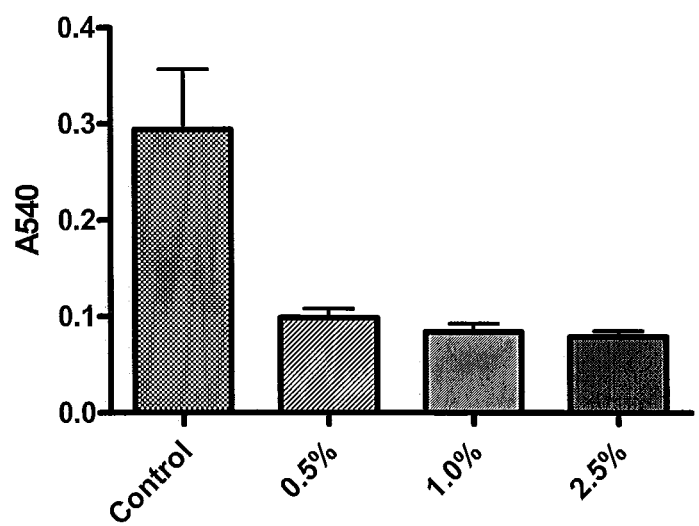
FIG. 11 is a histogram showing the effect of acetic acid on growth of *T. interdigitale;*

The inhibition of growth of *T. interdigitale* by acetic acid was assessed by establishing fungal growth experiments as per the materials and methods section. *T. interdigitale* cultures were either grown untreated or treated with 3 different concentrations of acetic acid at 30° C. for 96 hours (FIG. 11). This illustrates that there is a significant effect of 0.5% acetic acid the same concentration as was used with Peptides 1-4 previously as solvent. This experiment together with the lack of activity of Peptide 3 in the absence of acetic acid suggests that Peptide 4 is the most active compound against *Trichophyton* spp.

Effect of Poly-L-Lysine on *T. interdigitale* Growth

Figure 12:
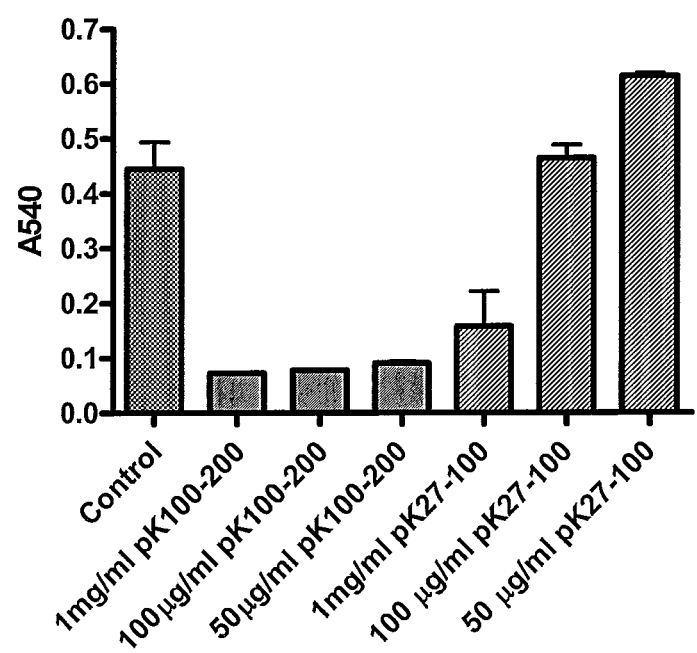
FIG. 12 is a histogram showing the effect of polylysine on *T. interdigitale* growth.

As Peptide 4 is a highly cationic peptide comprising lysine and arginine residues, the antifungal activity of poly-L forms of these amino acids was tested against *T. interdigitale* using growth inhibition assays as detailed in materials and methods in the absence of acetic acid. Control, untreated *T. interdigitale* cultures and those containing between 1 mg/ml and 50 µg/ml of poly-L-Lysine molecules ranging from 27-100 residues and 100-200 residues in length were established. Growth of the *T. interdigitale* in each culture was assessed after 96 hours at 30° C. Both sizes of poly-L-Lysine molecules inhibited the growth of the *T. interdigitale* (FIG. 12) but whereas the larger molecule inhibited growth at all concentrations tested, inhibitory activity was seen with the molecule of 27-100 amino acids in length only at higher concentrations (FIG. 12). This suggests that growth inhibition effects of Lysine on *Trichophyton* spp. is both size and dose-dependent.

Effects of Poly-L-Arginine and Poly-L-Lysine on the Growth of *T. rubrum*

Figure 13:
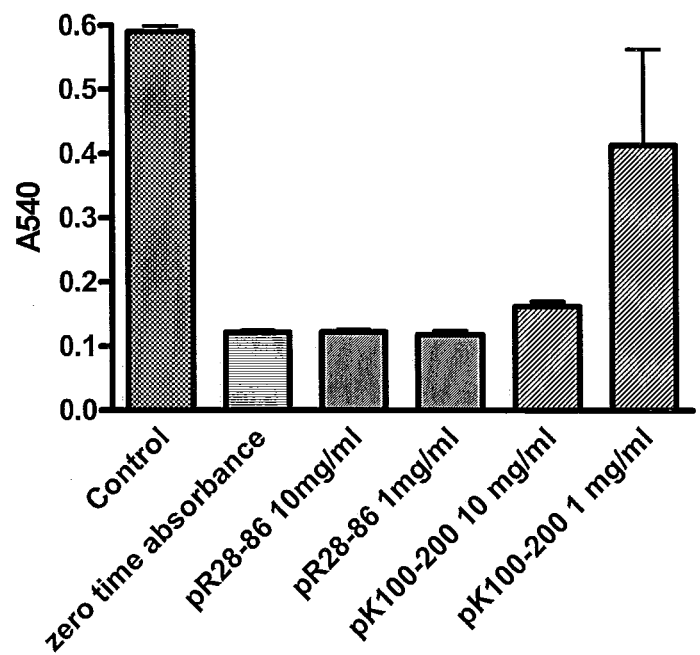
FIG. 13 is a histogram showing the effects of polylysine and polyarginine on the growth of *T. rubrum;*

The antifungal activity of poly-L-Arginine versus poly-L-Lysine was then tested against *T. rubrum*. The inhibition of growth was determined as per materials and methods in the absence of acetic acid. *T. rubrum* was cultured in medium alone, in medium containing poly-L-Arginine (28-86 amino acids in length) and poly-L-Lysine (100-200 amino acids). An uninoculated medium only control was also established. Cultures were maintained and growth monitored for 96 hours at 30° C. Poly-L-Arginine and poly-L-Lysine both inhibited the growth of *T. rubrum* (FIG. 13). Poly-L-Arginine was more active in its inhibitory impact against *T. rubrum* than poly-L-Lysine when tested at equivalent doses, totally inhibiting growth at 1 mg/ml (FIG. 13).

Inhibition of *T. interdigitale* and *T. rubrum* by poly-L-Arginine

Figure 14:
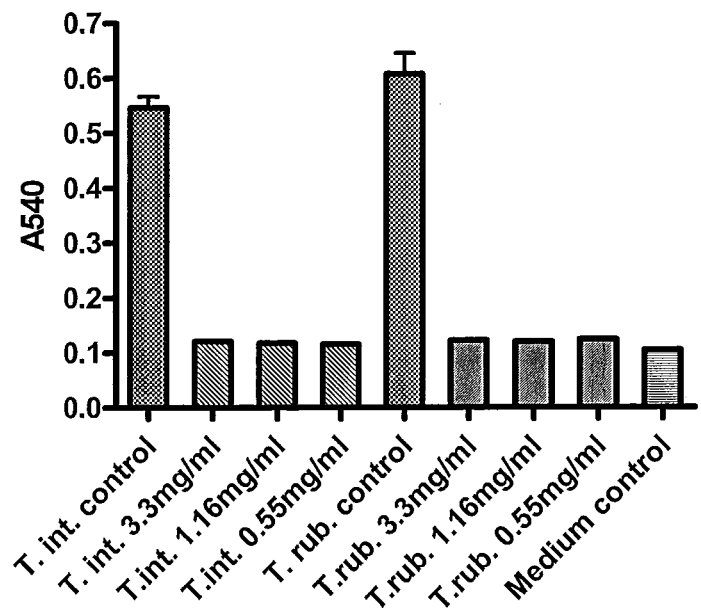
FIG. 14 is a histogram showing the inhibition of *T. interdigitale* and *T. rubrum* by poly-L-arginine.

The inhibition of growth of *Trychophyton* spp. by poly-L-Arginine was tested by setting up fungal growth experiments as per the materials and methods section. *T. rubrum* and *T. interdigitale* cultures were either grown in medium alone or in medium containing 3 different concentrations of poly-L-Arginine. No acetic acid was present in any samples. Medium controls were used to illustrate background absorbance of the media. Growth of the fungus was determined by the OD as described previously after 96 hours of incubation at 30° C. (FIG. 14). Polyarginine is seen to be active against both species of fungi down to 0.55 mg/ml (FIG. 14).

Effect of Reduced Concentration (100 µg/ml) of Polyarginine on *T. rubrum* and *T. interdigitale*

Figure 15:
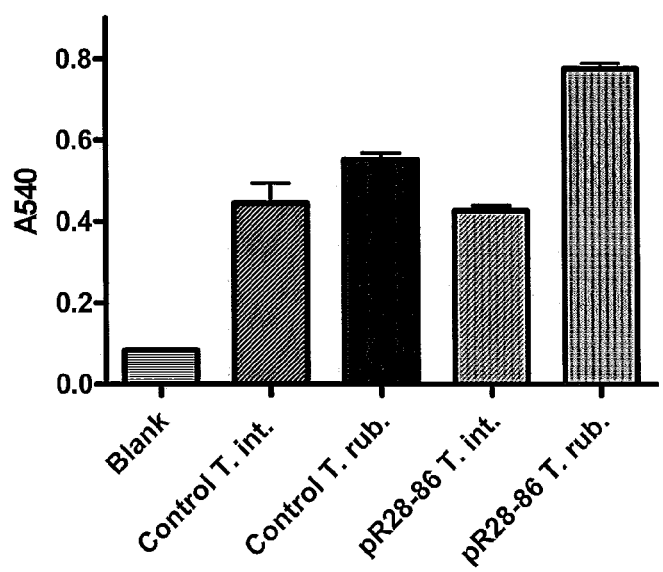
FIG. 15 is a histogram showing the effect of a reduced concentration of polyarginine on *T. rubrum* and *T. interdigitale;*

The inhibition of growth of *Trychophyton* spp. by polyarginine was tested by setting up fungal growth experiments as per the materials and methods section. *T. rubrum* and *T. interdigitale* cultures were either grown untreated or treated with a single concentration of polyarginine (100 µg/ml), with no acetic acid present in any samples. Medium controls were used to illustrate background absorbance of the media. Growth of the fungus was determined by the OD as described previously after 96 hours of incubation at 30° C. (FIG. 15). The reduced concentration leads to a loss of activity, this illustrates the dose effect of the polyarginine on the *Trychophyton* spp.

The Effect of Peptide Trimers (3 Amino Acids) on the Growth of *T. rubrum*

Figure 16:
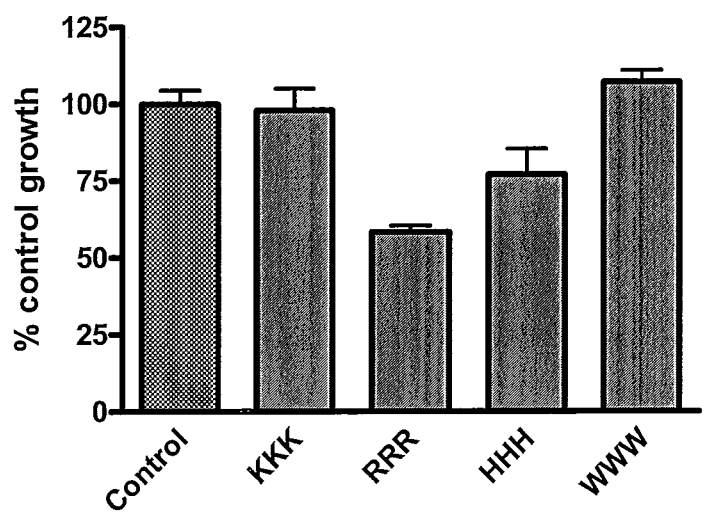
FIG. 16 is a histogram showing the effect of trimers on the growth of *T. rubrum;*

The activity of peptide trimers of poly-L-Lysine, poly-L-Arginine, poly-L-Histidine and poly-L-Tryptophan on the growth of *T. rubrum* was tested. The inhibition of growth was set up as per the materials and methods and *T. rubrum* was either left untreated or exposed to 2 mg/ml of each of the trimers. Cultures were maintained for 96 hours at 30° C. Fungal growth was measured by OD and the results displayed as a percentage of the growth in the untreated culture (FIG. 16). Poly-L-Arginine was the most active peptide against *T. rubrum* with only a 3 amino acid polypeptide required to elicit a significant reduction in growth of *T. rubrum*.

Effect of Peptide 4 (1.2 mg/ml) and NaCl on Growth of *T. interdigitale*

Figure 17:
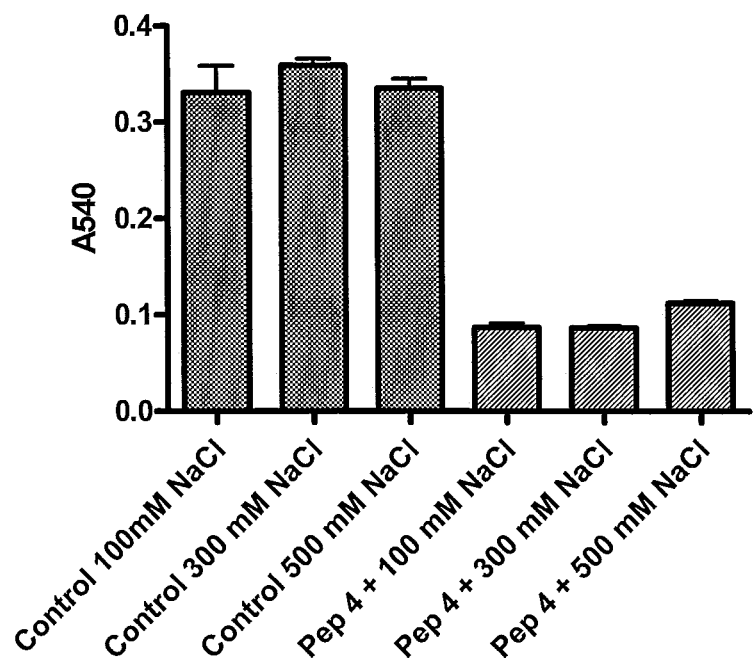
FIG. 17 is a histogram showing the effect of Peptide 4 and NaCl on the growth of *T. interdigitale;*

The impact of various salt concentrations on the antifungal activity of Peptide 4 towards *T. interdigitale* was investigated. *T. interdigitale* growth inhibition assays were set up as per the materials and methods in the absence of acetic acid. Cultures were left untreated or exposed to Peptide 4 plus a range of NaCl concentrations from 100 mM to 500 mM. *T. interdigitale* cultures were maintained for 96 h at 30° C. and growth assessed by OD as described previously (FIG. 17). The antifungal activity of Peptide 4 was not affected by to salt concentrations close to or in excess of those found under physiological conditions (FIG. 17). The antimicrobial activities of endogenous β-defensins are well-reported as being inhibited by even low salt concentrations.

Effect of Peptide 4 Against *Candida albicans* at High Salt Concentrations

Figure 18:
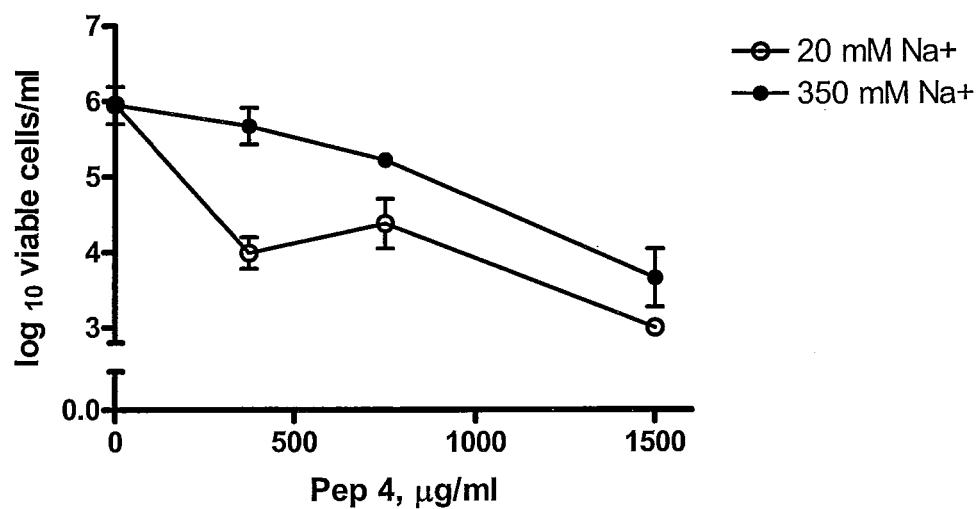
FIG. 18 is a graph showing the effect of Peptide 4 on *Candida albicans* at increased salt concentrations.

Survival of *C. albicans* was assessed as detailed in methods and materials following a 2 h incubation at 37° C. with a range of concentrations of Peptide 4. Two concentrations of NaCl were introduced into the growth medium to ascertain the impact of physiological and very high salt conditions (known to inhibit endogenous β-defensin peptide activity). Significant killing activity of Peptide 4 was observed at even very high salt concentrations (FIG. 18). As the concentration of Peptide 4 is increased it can be seen that the impact of the higher salt concentration is reduced (FIG. 18). Therefore, the fungicidal activity of Peptide 4 is not inhibited by salts.

Activity of Poly-L Lysine, Poly-D-Lysine and Poly-D-Arginine Against *Candida albicans*

Figure 19:
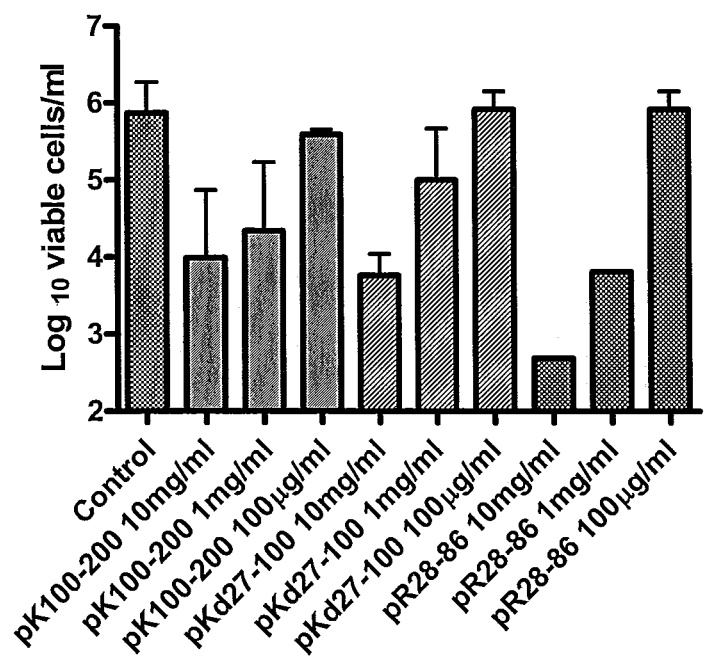
FIG. 19 is a histogram showing the effects of polylysine and polyarginine on the survival of *Candida albicans*.

The antifungal activity of poly-L Arginine versus Lysine and poly-L versus poly-D Lysine was assessed in order to determine, which if any of these peptide variants demonstrated enhanced activity against *Candida albicans*. *Candida* spp. was incubated as described in the materials and methods section for 2 hours at 37° C. in the presence of 100 µg/ml, 1 mg/ml and 10 mg/ml poly-D-lysine, poly-L-lysine and poly-L-Arginine. Survival was assessed as detailed previously and demonstrates increased antifungal activity of poly-L-Arginine over the poly-L-lysine (FIG. 19). It also demonstrates that the poly-D-lysine has very similar antifungal activity to the poly-L-lysine.

The invention claimed is:

1. A method for the treatment of a bacterial infection in a subject, comprising administering to the subject a peptide, or pharmaceutically acceptable salt thereof, wherein the peptide comprises 100 to 200 contiguous lysine residues and the bacterial infection is caused by a pathogen selected from the group consisting of: *Staphylococcus spp.; Pseudomonas spp.;* and *Propionibacterium spp.*

2. The method of claim 1, wherein the subject is a mammal.

3. The method of claim 2, wherein the mammal is a human.

4. The method of claim 1, wherein the subject is a bird.

5. The method of claim 1, wherein the bacterial infection is a dermal infection.

6. The method of claim 1, wherein the bacterial infection is caused by a pathogen selected from the group consisting of: *Staphylococcus aureus;* and *Staphylococcus epidermidis.*

7. The method of claim 1, wherein the peptide, or pharmaceutically acceptable salt thereof, is administered by a route selected from the group consisting of: oral, parenteral, rectal, dermal, transdermal, intrathoracic, intrapulmonary, and intranasal routes.

8. The method of claim 1, wherein the peptide, or pharmaceutically acceptable salt thereof, is formulated for topical administration.

9. A method for the treatment of a bacterial infection in a subject, comprising administering to the subject a peptide, or pharmaceutically acceptable salt thereof, wherein the peptide consists of 100 to 200 contiguous lysine residues and the bacterial infection is caused by a pathogen selected from the group consisting of: *Staphylococcus spp.; Pseudomonas spp.;* and *Propionibacterium spp.*

10. The method of claim 9, wherein the subject is a mammal.

11. The method of claim 10, wherein the mammal is a human.

12. The method of claim 9, wherein the subject is a bird.

13. The method of claim 9, wherein the bacterial infection is a dermal infection.

14. The method of claim 9, wherein the bacterial infection is caused by a pathogen selected from the group consisting of: *Staphylococcus aureus;* and *Staphylococcus epidermidis.*

15. The method of claim 9, wherein the peptide, or pharmaceutically acceptable silt thereof, is administered by a route selected from the group consisting of oral, parenteral, rectal, dermal, transdermal, intrathoracic, intrapulmonary, and intranasal routes.

16. The method of claim 9, wherein the peptide, or pharmaceutically acceptable salt thereof, is formulated for topical administration.

* * * * *

SEQUENCE LISTING

<160> NUMBER OF SEQ ID NOS: 10

<210> SEQ ID NO 1
<211> LENGTH: 31
<212> TYPE: PRT
<213> ORGANISM: Artificial
<220> FEATURE:
<223> OTHER INFORMATION: synthetic peptide

<400> SEQUENCE: 1

Cys Gly Gly Gly Gly Gly Cys Gly Gly Gly Cys Gly Gly
1               5                   10                  15

Gly Gly Gly Gly Gly Gly Cys Gly Gly Gly Gly Gly Gly Cys Cys
            20                  25                  30

<210> SEQ ID NO 2
<211> LENGTH: 31
<212> TYPE: PRT
<213> ORGANISM: Artificial
<220> FEATURE:
<223> OTHER INFORMATION: synthetic peptide

<400> SEQUENCE: 2

Cys Leu Leu Leu Leu Leu Cys Leu Leu Leu Leu Cys Leu Leu Leu
1               5                   10                  15

Leu Leu Leu Leu Leu Leu Cys Leu Leu Leu Leu Leu Leu Cys Cys
            20                  25                  30

<210> SEQ ID NO 3
<211> LENGTH: 31
<212> TYPE: PRT
<213> ORGANISM: Artificial
<220> FEATURE:
<223> OTHER INFORMATION: synthetic peptide

<400> SEQUENCE: 3

Cys Leu Gly Leu Gly Leu Gly Cys Gly Leu Gly Leu Cys Leu Gly Leu
1               5                   10                  15

Gly Leu Gly Leu Gly Leu Cys Gly Leu Gly Leu Gly Leu Cys Cys
            20                  25                  30

<210> SEQ ID NO 4
<211> LENGTH: 31
<212> TYPE: PRT
<213> ORGANISM: Artificial
<220> FEATURE:
<223> OTHER INFORMATION: synthetic peptide

<400> SEQUENCE: 4

Cys Arg Lys Arg Lys Arg Arg Cys Arg Lys Arg Lys Cys Lys Arg Lys
1               5                   10                  15

Arg Lys Arg Lys Arg Lys Cys Arg Lys Arg Lys Arg Lys Cys Cys
            20                  25                  30

<210> SEQ ID NO 5
<211> LENGTH: 7
<212> TYPE: PRT
<213> ORGANISM: Artificial
<220> FEATURE:
<223> OTHER INFORMATION: synthetic peptide

<400> SEQUENCE: 5

Lys Lys Lys Lys Lys Lys Lys
1               5

<210> SEQ ID NO 6
<211> LENGTH: 7
<212> TYPE: PRT
<213> ORGANISM: Artificial
<220> FEATURE:
<223> OTHER INFORMATION: synthetic peptide

<400> SEQUENCE: 6

Arg Arg Arg Arg Arg Arg Arg
1               5

<210> SEQ ID NO 7
<211> LENGTH: 40
<212> TYPE: PRT
<213> ORGANISM: Artificial
<220> FEATURE:
<223> OTHER INFORMATION: synthetic peptide

<400> SEQUENCE: 7

Gly Gly Gly Gly Gly Gly Gly Cys Gly Gly Gly Gly Gly Gly Cys Gly
1               5                   10                  15

Gly Gly Gly Cys Gly Gly Gly Gly Gly Gly Gly Gly Cys Gly Gly
            20                  25                  30

Gly Gly Gly Gly Cys Cys Gly Gly
        35                  40

<210> SEQ ID NO 8
<211> LENGTH: 40
<212> TYPE: PRT
<213> ORGANISM: Artificial
<220> FEATURE:
<223> OTHER INFORMATION: synthetic peptide

<400> SEQUENCE: 8

Leu Leu Leu Leu Leu Leu Leu Cys Leu Leu Leu Leu Leu Leu Cys Leu
1               5                   10                  15

Leu Leu Leu Cys Leu Leu Leu Leu Leu Leu Leu Leu Cys Leu Leu
            20                  25                  30

Leu Leu Leu Leu Cys Cys Leu Leu
        35                  40

<210> SEQ ID NO 9
<211> LENGTH: 40
<212> TYPE: PRT
<213> ORGANISM: Artificial
<220> FEATURE:
<223> OTHER INFORMATION: synthetic peptide

<400> SEQUENCE: 9

Gly Leu Gly Leu Gly Leu Gly Cys Leu Gly Leu Gly Leu Gly Cys Gly
1               5                   10                  15

Leu Gly Leu Cys Leu Gly Leu Gly Leu Gly Leu Gly Leu Cys Gly Leu
            20                  25                  30

Gly Leu Gly Leu Cys Cys Leu Gly
        35                  40

<210> SEQ ID NO 10
<211> LENGTH: 42
<212> TYPE: PRT
<213> ORGANISM: Artificial
<220> FEATURE:
<223> OTHER INFORMATION: synthetic peptide

<400> SEQUENCE: 10

```
Lys Arg Lys Arg Lys Arg Lys Cys Arg Lys Arg Lys Arg Arg Cys Arg
1               5                   10                  15
Lys Arg Lys Cys Lys Arg Lys Arg Lys Arg Lys Arg Lys Cys Arg Lys
                20                  25                  30
Arg Lys Arg Lys Cys Cys Arg Arg Lys Lys
            35                  40
```